(12) United States Patent
Hirshberg

(10) Patent No.: US 10,653,876 B2
(45) Date of Patent: May 19, 2020

(54) FAT REMOVAL DEVICE AND OBESITY TREATMENT

(71) Applicant: David Hirshberg, Haifa (IL)

(72) Inventor: David Hirshberg, Haifa (IL)

(*) Notice: Subject to any disclaimer, the term of this patent is extended or adjusted under 35 U.S.C. 154(b) by 907 days.

(21) Appl. No.: 15/201,632

(22) Filed: Jul. 5, 2016

(65) Prior Publication Data
US 2017/0021150 A1    Jan. 26, 2017

Related U.S. Application Data

(62) Division of application No. 13/426,684, filed on Mar. 22, 2012, now Pat. No. 9,409,006.

(60) Provisional application No. 61/473,779, filed on Apr. 10, 2011.

(51) Int. Cl.
| | |
|---|---|
| *A61M 5/32* | (2006.01) |
| *A61M 37/00* | (2006.01) |
| *A61M 1/00* | (2006.01) |
| *A61B 18/04* | (2006.01) |
| *A61B 18/18* | (2006.01) |

(52) U.S. Cl.
CPC ......... *A61M 37/0015* (2013.01); *A61B 18/04* (2013.01); *A61B 18/18* (2013.01); *A61M 1/0023* (2013.01); *A61M 37/0092* (2013.01); *A61M 2037/003* (2013.01); *A61M 2037/0023* (2013.01); *A61M 2037/0053* (2013.01); *A61M 2037/0061* (2013.01); *A61M 2202/08* (2013.01)

(58) Field of Classification Search
CPC ...... A61B 2018/00464; A61M 1/0023; A61M 2037/003; A61M 37/0015
See application file for complete search history.

(56) References Cited

U.S. PATENT DOCUMENTS

| | | | |
|---|---|---|---|
| 2002/0120261 A1* | 8/2002 | Morris | A61B 18/1477 606/41 |
| 2005/0228313 A1* | 10/2005 | Kaler | A61B 5/14514 600/583 |
| 2008/0234563 A1* | 9/2008 | Regittnig | A61B 5/14503 600/365 |
| 2012/0150266 A1* | 6/2012 | Shalev | A45D 44/22 607/99 |

\* cited by examiner

Primary Examiner — Matthew F Desanto

(57) ABSTRACT

A medical device for treatment for overweight or obesity is presented. The medical device is attached or implanted in patient's target body organs, wherein in each one of the device attachments, or daily in the case of long continuous attachment, the device removes up to 100 grams of energy containing materials from the body. The medical device optionally contains needles or alternatively contains crawling worm-like arm. The energy containing materials may be fat cells, fatty acid molecules driven out from the fat cells or lipids or carbohydrates molecules such as glucose from the blood stream.

34 Claims, 24 Drawing Sheets

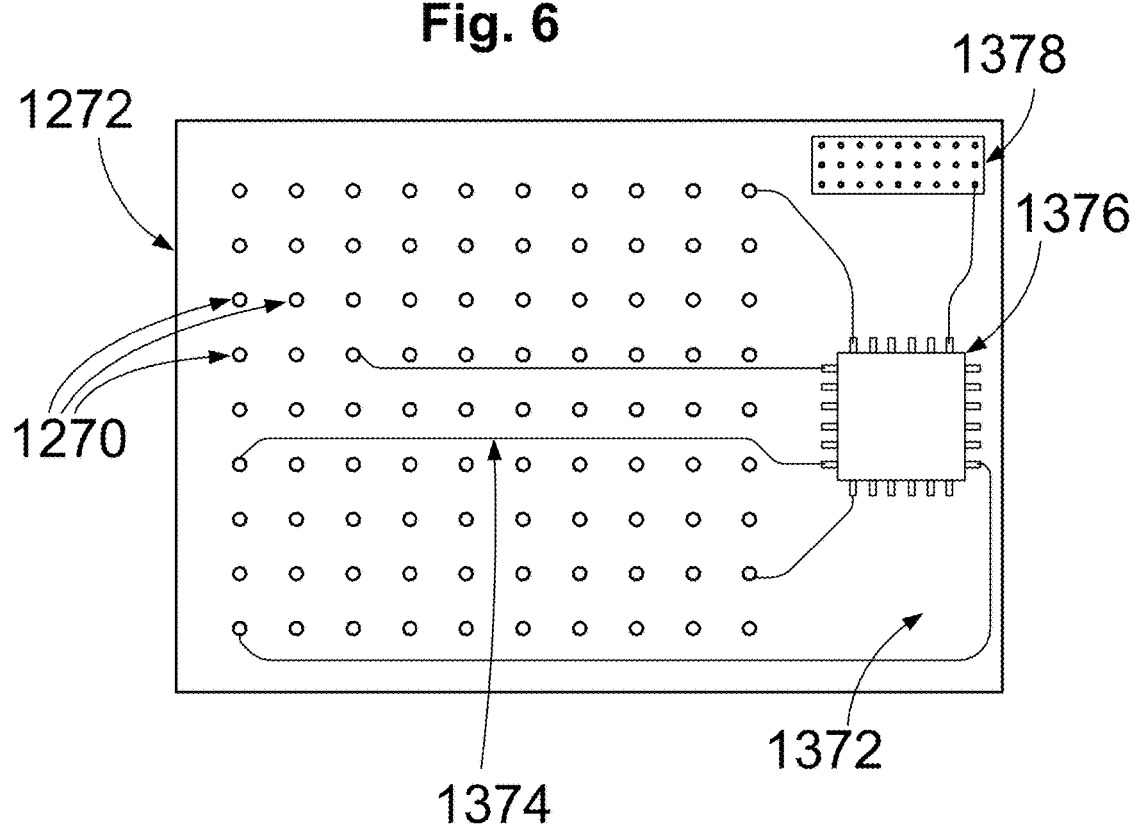
Fig. 6
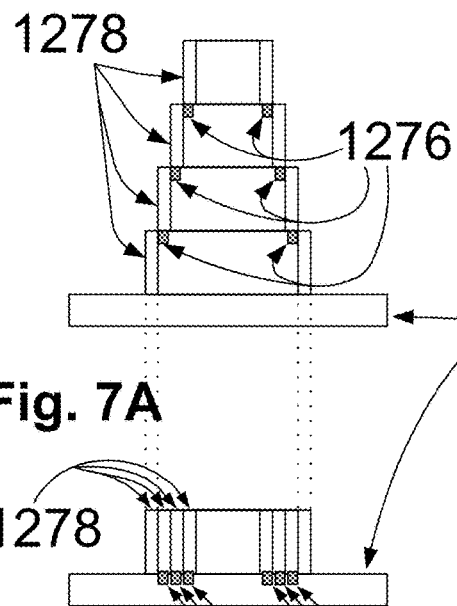
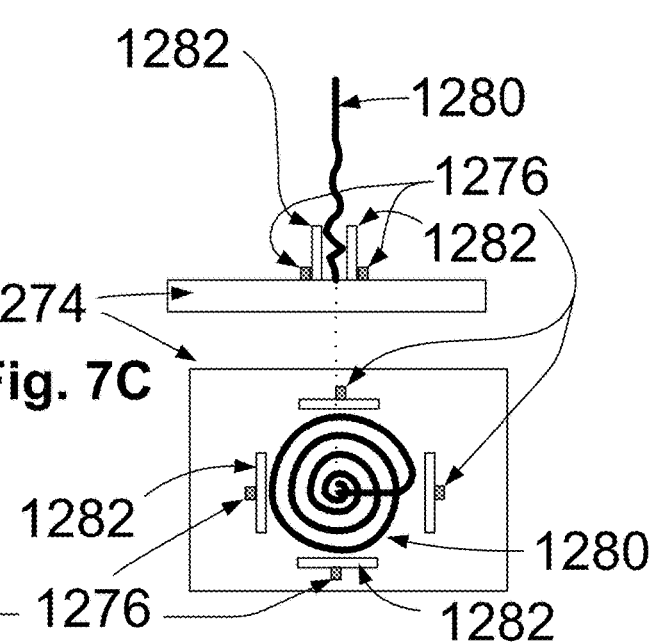
Fig. 7B, Fig. 7A, Fig. 7D, Fig. 7C

FAT REMOVAL DEVICE AND OBESITY TREATMENT

RELATED APPLICATION

This application is a divisional application of patent application Ser. No. 13/426,684 filed Mar. 22, 2012 Mar. 22, 2012 which is a non-provisional patent application of provisional patent application Ser. No. 61/473,779 filed Apr. 10, 2011.

FIELD AND BACKGROUND OF THE INVENTION

The present invention, in some embodiments thereof, relates to obesity treatment and, more particularly, but not exclusively, to liposuction and fat removal treatments.

Excess body weight is now widely recognized as one of today's leading health threats in most countries around the world and as a major risk factor for type 2 diabetes, cardiovascular disease, certain types of cancer and hypertension. Recent studies show that on average, obesity reduces life expectancy by six to seven years. A BMI of 30-35 reduces life expectancy by two to four years, while severe obesity (BMI>40) reduces life expectancy by 10 years.

Conservative treatment for obesity consists of dieting and physical exercise. However, due to the low success rate, medical treatments are extensively explored. Both medication and surgeries treatments are being used.

Most current medication treatments work by suppressing the appetite or decreasing absorption of fats eaten. Apart from its questionable success, current available medication suffers from major side effects and many medication did not get FDA approval or withdrawn from the market by the FDA after new risks and side effects revealed after FDA approval.

Surgical procedure are divided to bariatric surgeries that reduce the capacity or the opening of the stomach and liposuction, in many cases, considered more as a cosmetic surgery, that remove fat from many different sites on the human body such as abdomen, hips, thighs etc. Both types of surgeries are risky and have side effects and are not recommend for non extreme cases in general.

It is well recognized that new effective, less expensive, less risky and with as less as possible side effects obesity treatment are highly required.

The present invention addresses the issues of obesity by introducing a new type of medical treatment performed by a matching medical device.

SUMMARY OF THE INVENTION

The present invention is an obesity preventive treatment concept for fat removal which is different from a standard liposuction procedure.

According to an aspect of some embodiments of the present invention there is provided a local area, small amount repetitive fat removal treatment is used. The fat removal treatment removes a fat tissue or other energy containing materials ranges from 1 to 100 gram of fat or equivalent in each treatment.

According to an aspect of some embodiments of the present invention there is provided a treatment that removes a fat tissue under skin area ranges from 1 to 100 squared centimeters and with less then 30% of the fat in that area in each treatment. Alternatively, treatment removes the fat from the blood stream from blood vessel under the skin area.

According to an aspect of some embodiments of the present invention there is provided a treatment that is not a surgical procedure and performed independently by the patient. Alternatively or additionally treatment can be given by paramedical or cosmetic institutes.

According to an aspect of some embodiments of the present invention there is provided, the treatment in the present invention is performed using a special medical device designed to perform the treatment. This device hereinafter is referred as fat removal device. The fat removal device removes not only fats but any energy containing materials comprising molecules including lipids (fats) which include but not limited to fatty acids and triglycerides and carbohydrates which include but not limited to glucose, fructose and ketones or any molecule that the human body transfer to a molecule that the human body cells are using as a source of energy.

According to an aspect of some embodiments of the present invention there is provided a fat removal treatment that is performed using a device that is attached to a target area of the body. The fat tissue that present under the skin area that under the device is the target tissue for fat removal and there is no need for any other human operation, mechanical or another, to direct the device to the target fat tissue or to help in any other way to the fat removal treatment.

According to an aspect of some embodiments of the present invention there is provided a method for treatment for obesity comprising repetitive attachments of a medical device to a different patient's target body organs, wherein in each one of the device attachments, the device removes up to 100 grams of energy containing materials from the body.

According to some embodiments of the invention, the medical device comprises needles penetrating the skin and sucks a fat tissue in said target body organ.

According to some embodiments of the invention, the medical device melts a fat tissue in said target body organ and then removes said fat tissue.

According to some embodiments of the invention, the medical device injects material to target body organ.

According to some embodiments of the invention, the medical device measures said target body organ.

According to some embodiments of the invention, the needles are folded in said medical device before treatment and opens during said treatment.

According to some embodiments of the invention, the medical device is adhesive patch.

According to some embodiments of the invention, the medical device comprises of worm-like arm that penetrate the skin and crawl in to the fat tissue.

According to some embodiments of the invention, the energy containing materials are fat cells.

According to some embodiments of the invention, the energy containing materials are fatty acids molecules.

According to some embodiments of the invention, the energy containing materials are glucose molecules.

According to some embodiments of the invention, the medical device drives fat cells to release fatty acids.

According to some embodiments of the invention, the medical device remove said energy containing materials from the blood stream.

According to an aspect of some embodiments of the present invention there is provided a medical device for non surgical, patient self treatment for obesity, wherein the device is attached to a patient's target body organ and in each device attachment, the device removes up to 100 grams of energy containing materials from the body.

According to some embodiments of the invention, the medical device comprises needles penetrating the skin and sucks the fat tissue in said target body organ.

According to some embodiments of the invention, the medical device melts a fat tissue in said target body organ and then removes said fat tissue.

According to some embodiments of the invention, the medical device injects material to target body organ.

According to some embodiments of the invention, the medical device measures said target body organ.

According to some embodiments of the invention, the needles are folded in said medical device before treatment and open during said treatment.

According to some embodiments of the invention, the medical device is an adhesive patch.

According to some embodiments of the invention, the medical device comprises of worm-like arm that penetrates the skin and crawls in to the fat tissue.

According to some embodiments of the invention, the energy containing materials are fat cells.

According to some embodiments of the invention, the energy containing materials are fatty acids molecules.

According to some embodiments of the invention, the energy containing materials are glucose molecules.

According to some embodiments of the invention, the medical device drives fat cells to release fatty acids.

According to some embodiments of the invention, the medical device removes said energy containing materials from the blood stream.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a controller, such as a computing platform for executing a plurality of instructions. Optionally, the data processor includes a volatile memory for storing instructions and/or data and/or a non-volatile storage, for example, a solid state hard-disk and/or removable media, for storing instructions and/or data. Optionally, a network connection is provided as well. A display and/or a user input device such as a keyboard or touch screen are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 3A is an isometric view of the fat removal device;

FIG. 3B is an upper side isometric view of a disposable cartridge of the fat removal device;

FIG. 3C is a lower side isometric view of a disposable cartridge of the fat removal device;

FIG. 3D is a cross-section view of the fat removal device;

FIG. 3E is another cross-section view of the fat removal device;

FIG. 3F is an illustration of a penetration plan of a needle of the fat removal device;

FIG. 3G is another illustration of different penetration plan of the needle of the fat removal device;

FIG. 5A is a lower side isometric view of a disposable cartridge of the micro needles version of the fat removal device;

FIG. 5B is a cross-section view of the disposable cartridge of the micro needles version of the fat removal device;

FIG. 5C is a dynamic state varying cross-section view of the disposable cartridge of the micro needles version of the fat removal device;

FIG. 5D is a flowchart of the fat removal process of the micro needles version of the fat removal device in accordance with the disposable cartridge states;

FIG. 6 is a top view of micro needles PCB implementing electrical melting for the micro needles version of the fat removal device, in accordance with a preferred embodiment of the invention;

FIGS. 7A-7D are illustrations of other alternative versions of folded micro needles for the fat removal device, in accordance with a preferred embodiment of the invention;

FIG. 7A is a cross section view of a telescopic micro needle embodiment in close state;

FIG. 7B is a cross-section view of a telescopic micro needle embodiment in open state;

FIG. 7C is a top view of a spiral folded micro needle in close state;

FIG. 7D is an cross-section view of a spiral folded micro needle embodiment in open state;

FIG. 8A is an isometric view of the patch shape fat removal device;

FIG. 8B is a cross-section view of the patch shape fat removal device;

FIG. 8C is top view of an alternative shapes for the patch shape fat removal device;

FIG. 9A is an isometric view of the worm shape transport subsystem version of fat removal device;

FIG. 9B is a cross-section view of the worm shape transport subsystem version of fat removal device;

FIG. 9C is a cross-section view of s disposable cartridge of the worm shape transport subsystem version of fat removal device;

FIG. 9D is a cross-section view of the worm shape transport subsystem version of fat removal device during in body treatment;

FIG. 9E is an isometric view of the head of the worm shape transport subsystem version of fat removal device when its tip is closed;

FIG. 9F is an isometric view of the head of the worm shape transport subsystem version of fat removal device when its tip is opened;

FIG. 9G is a front view of the head of the worm shape transport subsystem version of fat removal device;

FIG. 9H is a cross-section view of the worm of the worm shape transport subsystem version of fat removal device;

FIG. 10A is an illustrative view of the initial injection phase of the non-destructive fat removal treatment;

FIG. 10B is an illustrative view of the diffusion phase of the non-destructive fat removal treatment;

FIG. 10C is an illustrative view of the fatty acid release phase of the non-destructive fat removal treatment;

FIG. 10D is an illustrative view of the suction phase of the non-destructive fat removal treatment;

FIG. 12A is a top view of the micro needle in close position;

FIG. 12B is a top view of the micro needle in open position;

FIG. 12C is a side view of the micro needle.

FIG. 12D is a detailed view of the needle transmission subsystem;

FIG. 13A is an inner view of the abdomen illustrates two options of implant installation positions and connections in a patient;

FIG. 13B is a conceptual block diagram of the implant device;

FIG. 14A is an illustrative view of the initial injection phase of the non-destructive fat removal treatment;

FIG. 14B is an illustrative view of the diffusion phase of the non-destructive fat removal treatment;

FIG. 14C is an illustrative view of the phase of fatty acid release and the decompose of the fatty acid using a chemical reactions in the intercellular fluid of the fat tissue; and FIG. 14D is an illustrative view of the phase of the removal of the chemical reaction products through the blood system.

DESCRIPTION OF SPECIFIC EMBODIMENTS OF THE INVENTION

Figure 1:
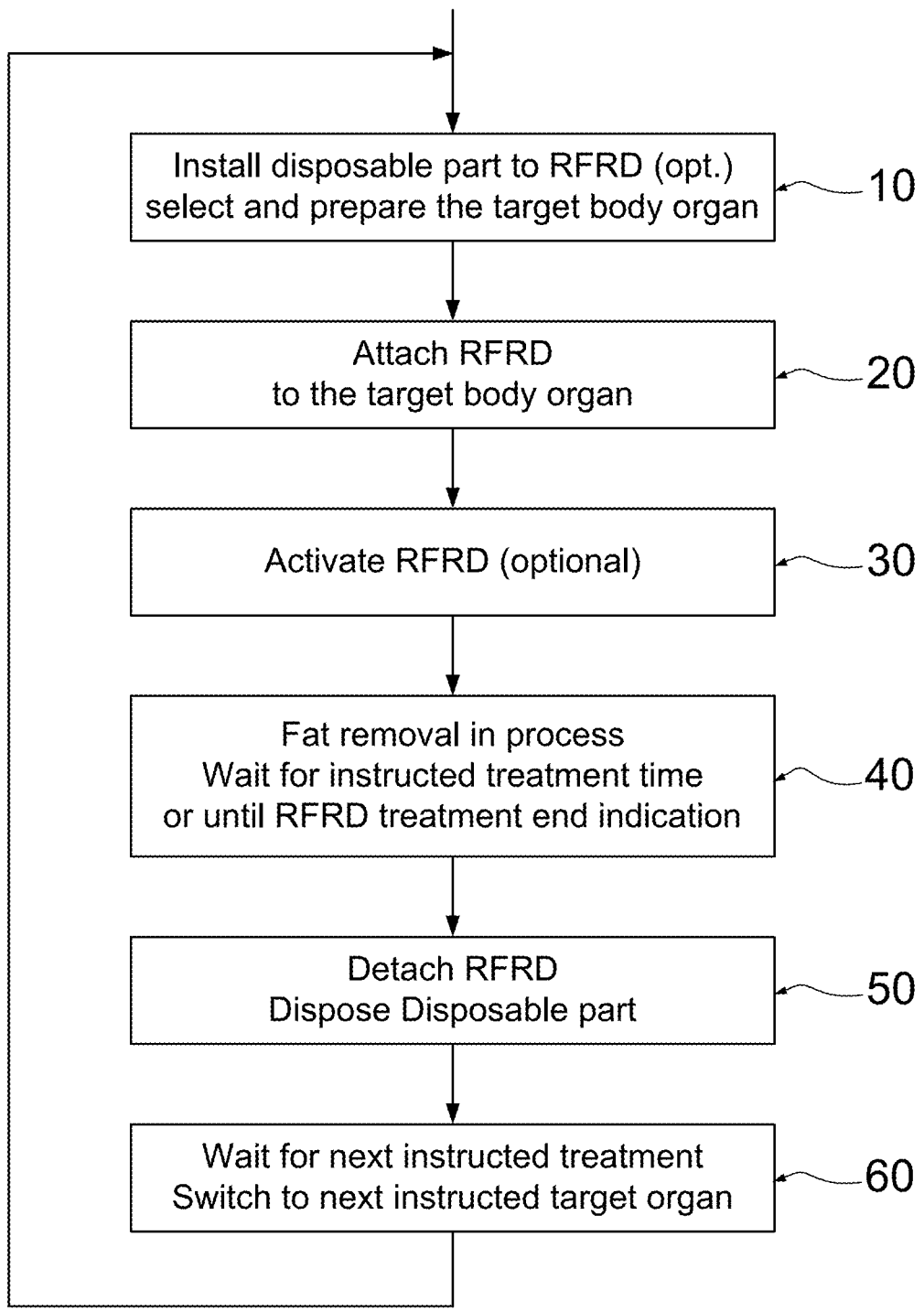
FIG. 1 is a flowchart of a fat removal treatment, in accordance with a preferred embodiment of the invention.

The present invention, in some embodiments thereof, relates to obesity treatment and, more particularly, but not exclusively, to a fat removal treatments.

Obesity is overweight state that obtained after a long duration of excessive energy intake over energy expenditure. The human body is very efficient energy conversion utilization and storage machine. Over a long period of evolution the availability of food was limited and human body developed a very efficient way to search and consume food, convert it and store it in to an energy reservoir, the fat tissues, and consume it efficiently. Many mechanism in the body starting from the psychological feelings such as hunger, continuing with the complex metabolism that start with efficient digestion that consume all energy contains in the food, and ending with the storage of the excessive energy in the fat tissue are all tuned to prepare the human body for survival in long period of food shortage.

Unfortunately when it comes to a situation that plenty of food is always available and energy consumption is degrading, the human body has no efficient mechanisms to avoid the unhealthy situation of excessive storage of available energy, i.e. obesity.

Because of the complexity of the processes involved in development of obesity, medication failed to successfully treat obesity. Many medications that trying to interfere with our hunger and brain activities that involve in the metabolic system lead to side effect as depression and even induce an significant increase in suicide rate.

Recognizing that any intervention in the process from hunger until the excessive energy is stored in the fat tissues is doomed to fail, the invention is focused on treatment in the last stage, i.e., to avoid excessive energy storage. In a typical case obese person increase its fat reservoirs with 3-30 gram of fat a day leading to 1-10 Kg of weight gain in a year. Obesity developed over several years and even decades accumulating tens of kilograms of fat tissues.

While the full mechanism of how the body decide where to store the energy in fat tissue is not fully understood, it is well known that some areas, such as abdomen and hips are more preferable. Moreover, the energy is stored in triglyceride molecules that are accumulated in the fat cells. Initially, to accumulating the triglyceride, the fat cells increase in size about fourfold up to about 0.2 mm in diameter and then the fat cells are dividing and increasing the absolute number of fat cells present in the body. Average adult has about 30 billion fat cells. When a person is gaining weight, he gets to the point where the number of fat cell increases. Those cells will not disappear when one losses the weight.

While most of the fat tissues, the energy reservoir, are located under our skin some fat, known as intra-abdominal fat, is located deep in abdomen surrounding our internal organs. Intra-abdominal fat is accumulated in later stages of gaining weight and believed to be more unhealthy fat tissue. Based on the above, there is a strong need to treat the obesity as early as possible.

Fortunately, the body energy reservoir is located in relatively accessible place under about 3 mm thick of skin tissue. A procedure to remove fat tissues, known as liposuction, is a surgical procedure that involves massive fat tissue removal. As much as 23 Kg of fat tissue removal was reported in a single liposuction in the past. A very large volume of fat removal is a complex and potentially life-threatening procedure. Current regulation does not recommend more than 5 liters removal. Liposuction is a surgical treatment performed as follows: (1) penetrating with a cannula of few millimeters in diameter the skin in a selected point, (2) hand movement of the cannula by a surgeon in the excessive fat tissues, (3) combining this movement on the tissue with a suction force removes the excessive fat tissues. Liposuction treatment is used when the patient is already very obese and does not use as preventive treatment.

Due to the severe side effects liposuction it not a recommended treatment for obesity but it is a popular as a cosmetic treatment where less fat volume need to be remove and the main goal is to sculpt the body shape. As alternative to liposuction and some time as an assistant to the liposuction procedure a fat melting treatment is performed. Fat melting involves disassembly and liquefying of the fat cells and tissues either to ease the suction or to encourage the body to remove the excessive fat by itself. Fat melting can be done by transmitting energy to the fat tissues using direct thermal heating, acoustic energy (ultrasound), RF waves as well as optical wave using lasers and optionally fiber optics.

Fat melting with out suctioning can help sculpting a specific target organ but is not healthy since most of the melted fat is not removed from the body. Most of those fats are just cycles in the blood and stored in other fat tissues in the body. The excessive fats and other molecules that are generated from the fat tissue melting create a harmful stress on the body metabolism.

The present invention is a new obesity preventive treatment concept different from a standard liposuction. In the present invention, a repetitive local area and small amount of fat removal treatment is used. The treatment removes a fat tissue or other energy containing materials ranges from 1 to 100 gram of fat or equivalent in each treatment. The treatment removes a fat tissue under skin area ranges from 1 to 100 squared centimeters and with less then 30% of the fat in that area in each treatment. Alternatively, treatment removes the fat from the blood stream in blood vessel under the skin area. The treatment is not a surgical procedure and performed independently by the patient. Alternatively or additionally treatment can be given by paramedical or cosmetic institutes. The treatment in the present invention is performed using a special device designed to perform the treatment. This device hereinafter is referred as a residual fat removal device or just a fat removal device or a micro liposuction device or in short RFRD. As used herein, the term/phrase residual fat removal treatment or in short, fat removal treatment or just fat removal, means a treatment with a residual fat removal device.

Fat in the context of residual "fat" removal device is referred not only to a fat removal but also to a removal of any energy containing materials or molecules including lipids (fats) which include but not limited to fatty acids and triglycerides and carbohydrates which include but not limited to glucose, fructose and ketones.

As used herein, the term/phrase energy containing molecules means any molecule that the human body cells are using as a source of energy or any molecule that the human body transfer to a molecule that the human body cells are using as a source of energy.

As used herein, the term/phrase energy containing materials means materials that include energy containing molecules such as fat cells, fat tissue, intercellular fluid or blood.

Unlike liposuction treatment, residual fat removal treatment is performed using a device that is attached to the target area of the body. The fat tissue that present under the skin area that under the device is the target tissue for fat removal and there is no need for any other human operation, mechanical or another, to direct the device to the target fat tissue or to help in any other way to the fat removal.

EXAMPLES

Reference is now made to the following examples, which together with the above descriptions illustrate some embodiments of the invention in a non limiting fashion.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

For purposes of better understanding some embodiments of the present invention, as illustrated in FIGS. 1-11 of the drawings, reference is first made to FIG. 1. FIG. 1 illustrates a flowchart of a residual fat removal treatment according to a preferred embodiment of the invention.

Residual fat removal treatment according to this invention is obesity prevention treatment and may be used in early stage of weight gain. In each treatment, a 1-100 gram of fat is removed from a target body organ. Treated area is a fat tissue under skin surface ranges from 1 to 100 squared centimeters. Alternatively, residual fat removal is performed from blood vessels located under the skin in the target body organ. The amount of fat reduction is selected by factors such as the state of overweight of the patient, the rate of weight gain before treatment the frequency of planed treatment as well as general patient medical and other conditions.

As used herein, the term/phrase target body organ means a specific area of skin on patient's body that the patient attached the RFRD to, and the fat removal is performed on the fat tissue or the blood vessels that are adjacent to that area.

In first step 10, the patient prepares the residual fat removal device to the treatment. In case there are disposable parts in the RFRD, patient install them. The patient also prepares the selected target body organ (e.g. hips, thighs) and exposes the skin of the target body organ.

In second step 20 the patient attaches the residual fat removal device to the first target body organ. In a preferred embodiment of the invention, the RFRD can be in the form of a patch and attached to the skin by adhesive materials. Additionally or alternatively the RFRD is attached to the organ using mechanical aims with support from adjacent body organ. For example, the RFRD may be attached to the belly using strips that surround the body or attached to a limb by wearing an elastic sock over RFRD.

In third step 30 the patient activates the RFRD to start the fat removal operation. Alternatively the RFRD starts its operation automatically as soon as the RFRD is being attached to the organ.

In the fourth step 40, fat removal is performed. The duration it takes to the residual fat removal device to suck the fats and complete single treatment is varying depending on the type of the device and the amount of fats to be removed. In a preferred embodiment of the invention, a patch type RFRD is used and the treatment time is overnight. The patient glues the patch before he goes to sleep and removes it in the morning. Alternatively, the fat removal treatment duration is few minutes to several hours. Optionally RFRD has an indicator to signal the patient that the treatment is finished. Indication may be visually or auditory or tactile or a combination of the above. RFRD is designed to induce minimum pain or discomfort for the patient.

After fat removal ends, step 50, patient detaches the RFRD from the target organ. In a preferred embodiment of the invention the RFRD is disposable and the patient dispose the RFRD and use a new RFRD in the next treatment. Alternatively, the RFRD device is multi-treatment device comprising (1) a disposal part that contains at least a sterile unit that comes in contact with the skin and a fat tank that accumulates the removed fat, and (2) a multi-treatment part.

Residual fat removal treatment is based on the idea that the treatment constantly using repeatedly frequently treatments, and gradually removes the excessive fat from the patient. In step 60, the patient wait for the next treatment according to the instruction he gets from the physician or RFRD manufacturer. In a preferred embodiment of the invention, the patient uses the residual fat removal treatment daily as long as the patient is above his target weight. Alternatively, treatment is done several times or once a week. Additionally or Alternatively the RFRD incorporate a timer that remind/instruct the patient on the next treatment time. Although residual fat removal is very gentle and incur minimal destruction to the body area of treatment. The skin and fat tissues need time to recover so in sequential treatments the patient uses different target organ in each treatment. In the preferred embodiment, the patient uses a predetermined cyclic plan that selects the target body organ for the next treatment. Additionally and alternatively, the RFRD has a build in plans and after and before each treatment the RFRD reminds/instructs the patient on the next treatment target body organ/area.

Figure 2:
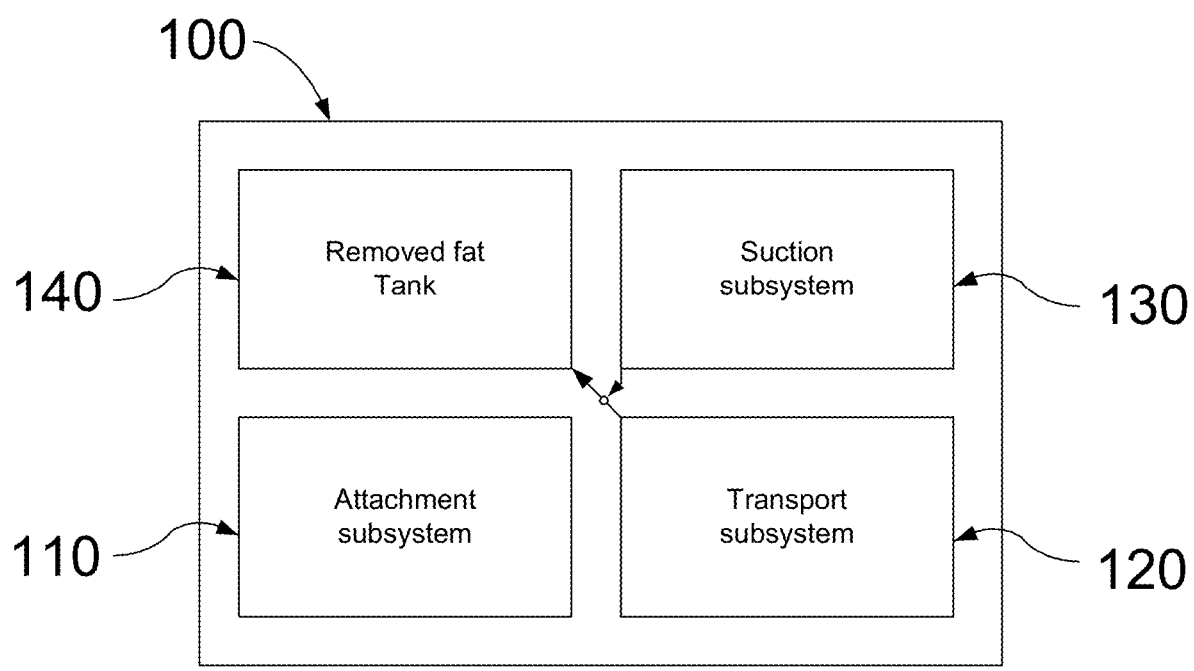
FIG. 2 is an elementary block diagram of the fat removal device, in accordance with a preferred embodiment of the invention.

Reference is now made to the elementary block diagram of the residual fat removal device as illustrated in FIG. 2. Residual fat removal device 100 comprising: an attachment subsystem 110, transport subsystem 120, suction subsystem 130 and Removed fat tank 140. Attachment subsystem 110 creates the bonding force between RFRD 100 and the target body organ. This bonding force ensure that RFRD 100 will not move or detach from body organ during the fat removal as well as give the sufficient backing force to allow the transport subsystem penetrates the skin and the suction subsystem suck the fat without any movement or displacement between RFRD and the patient's skin. The transport subsystem 120 is responsible for transferring the fats from the fat tissue to removed fat tank 140. Suction subsystem 130 generates the forces that drive the transit of the fats from the fat tissue to the removed fat tank 140.

Before explaining at least one embodiment of the invention in detail, it is to be understood that the invention is not necessarily limited in its application to the details of construction and the arrangement of the components and/or methods set forth in the following description and/or illustrated in the drawings and/or the examples. The invention is capable of other embodiments or of being practiced or carried out in various ways.

Figure 3A:
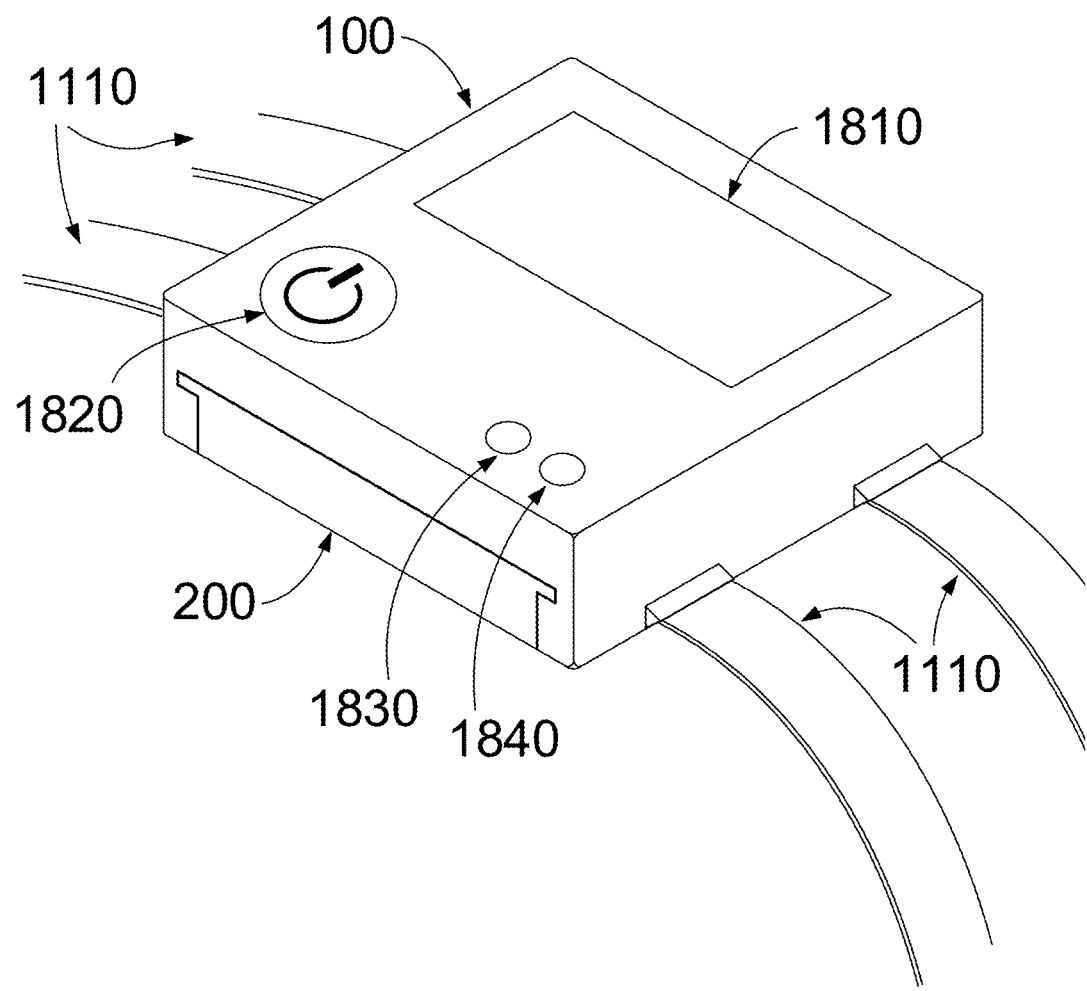
FIGS. 3A-3G are illustrations of an exemplary embodiment of a fat removal device in accordance with a preferred embodiment of the invention.

Many embodiments may be designed to implement this elementary system. In FIG. 3A-FIG. 3G an exemplary embodiment of the invention is illustrated. Reference is now made to FIG. 3A illustrates an isometric view of residual fat removal device. Residual fat removal device 100 comprises strips 1100 to attach RFRD 100 to the target body organ.

RFRD 100 has a start push button 1820 to start fat removal operation and two indication LEDs 1830 and 1840 to indicate RFRD 100 is in operation and finished treatment respectively. In addition RFRD 100 has a display 1810 to provide additional information to the patient. The information includes information on past, present and future treatments location of the patient body, past, present and future time and date of treatments as well as the amount of fat removed in each treatment. Residual fat removal device 100 comprises a disposable cartridge 200. Patient insert new cartridge 200 in each new treatment and dispose cartridge 200 when the treatment finished.

Figure 3B:
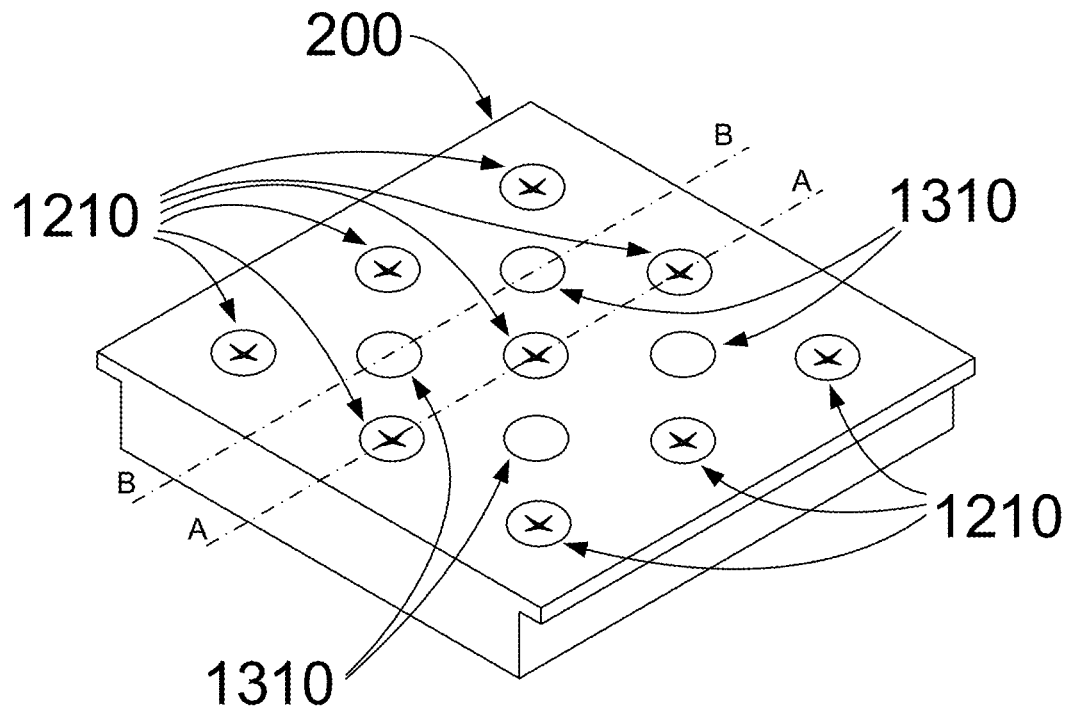
Figure 3C:
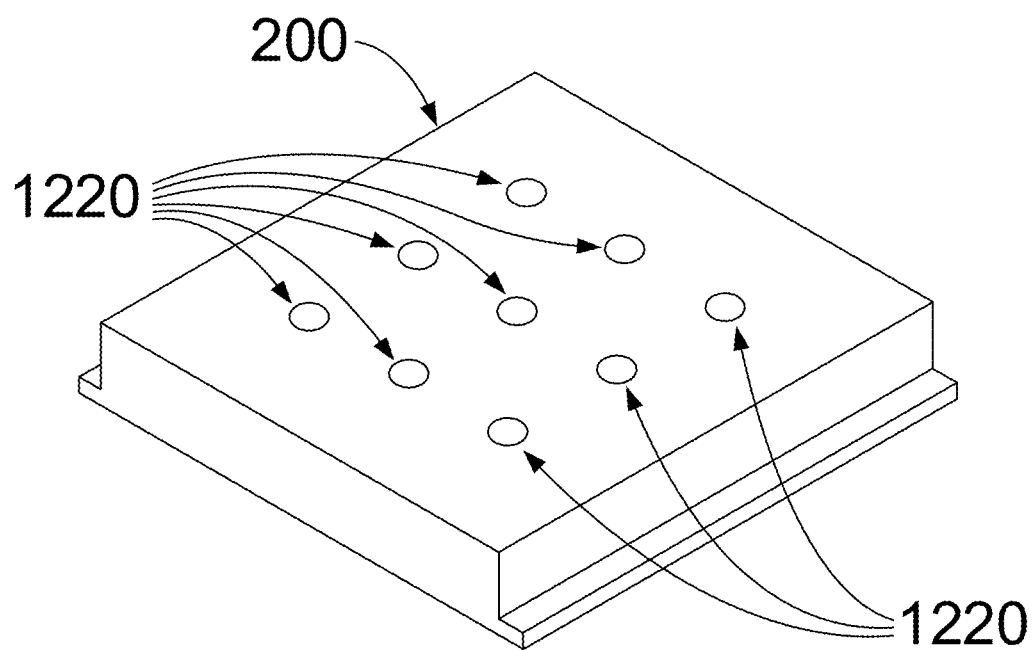

Reference is now made to FIG. 3B. In FIG. 3B an isometric upper view of disposable cartridge 200 is illustrated. The top side of the cartridge has nine needle guides 1210. Needle guides 1210 have a concave head that enables RFRD to push down and rotate Needle guides 1210. Scattered between needle guide 1210 there are four suction ports 1310. Reference is now made to FIG. 3C. FIG. 3C illustrates an isometric lower view of disposable cartridge 200. The lower side of the cartridge has nine needle outlets 1220. Needle outlet 1220 comprises a rubber pad that seals a hole in disposable cartridge 200 plastic case. Disposable cartridge 200 contains nine needles that are pushed down by RFRD 100 using the needle guides 1210. The needles pass through needle outlets 1220, penetrate the body skin and reach the fat tissue. The inner structure of the disposable cartridge 200 is illustrated in FIGS. 3D and 3e in two cross-sections indicated as A-A and B-B.

Figure 3D:
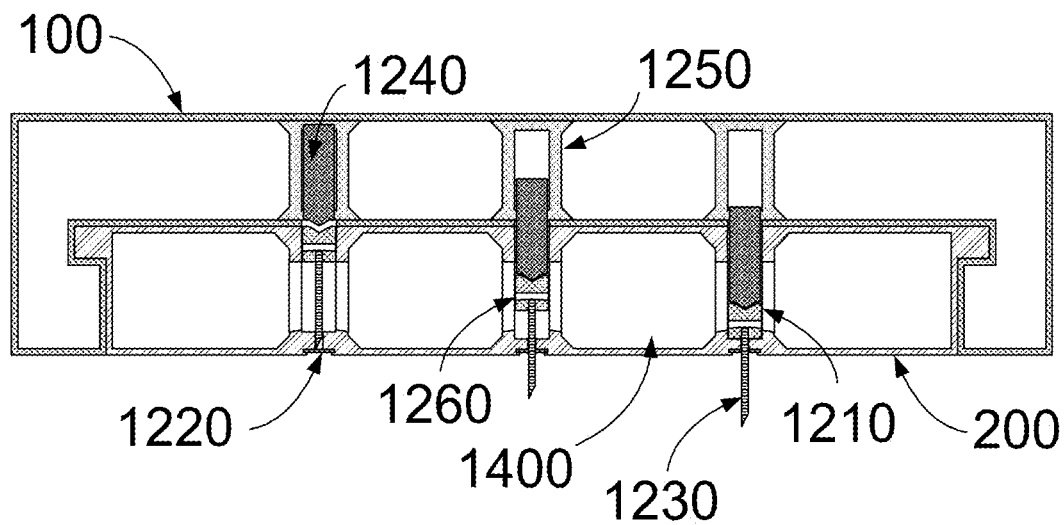

Reference is now made to FIG. 3D. FIG. 3D illustrates cross-section A-A view of residual fat removal device 100. RFRD 100 plastic case constitutes the top side of the device as well as surround and hold dispensable cartridge 200. The transport subsystem is based on nine needles 1230. In an exemplary embodiment of the invention, Needle 1230 is a standard stainless steel hypodermic needle. In order to cross the skin tissue and reach the fat tissue the needle length is between 4-6 mm. Needle 1230 width selected to minimize pain and tissue distraction and is less then 1 mm width. Gauge number of 20 to 34 may be used. In an exemplary embodiment of the invention, gauge number of 31 (Outer Diameter=0.2604 mm; Inner Diameter 0.133 mm) is used. When dispensable cartridge 200 is not in use, needles 1230 reside inside the cartridge (as illustrated by the left needle in the figure). When RFRD 100 starts micro fat removal treatment, it first insert needle 1230 to the skin. Insertion is performed by pushing needle guide 1210 downwards. The guide 1210 is pushed by an actuator 1240 which is driven by a miniature electromagnetic motor 1250. Motor 1250 controls the penetration depth of needle 1230. The penetration depth of the middle needle in FIG. 3D is half the maximum penetration depth. The penetration depth of the right needle in FIG. 3D is full penetration. Optionally, motor 1250 rotates needle 1230. In the cases the needle opening is directional (the common case) rotating of needle 1230 increase suction capacity. When fat removal ends, the needle is pulled up by stopping the force of actuator 1240. A spring (not shown in the illustration) pull needle 1230 back to its initial position in cartridge 200. Needle 1230 exits cartridge 200 through needle outlets 1220. Needle outlets 1220 is a sheet of rubber that keep cartridge 200 sealed to provide efficient suction of the fat. When suction is active, the fat is transferred from the fat tissue through hollow needle 1230. At the end of the needle the fat is reaching a hollow chamber 1260 located in needle guide 1210. Needle guide 1210 is a plastic part that plays three functions: (1) holds needle 1230, (2) transfer the movement and rotation control form actuator 1240, and (3)

transfer the sucked fat from needle 1230 top to removed fat tank 1400. The hollow chamber 1260 has openings enables the removed fat to be accumulated in the removed fat tank 1400. Removed fat tank 1400 occupies most of the volume of cartage 200 which is hollow.

Figure 3E:
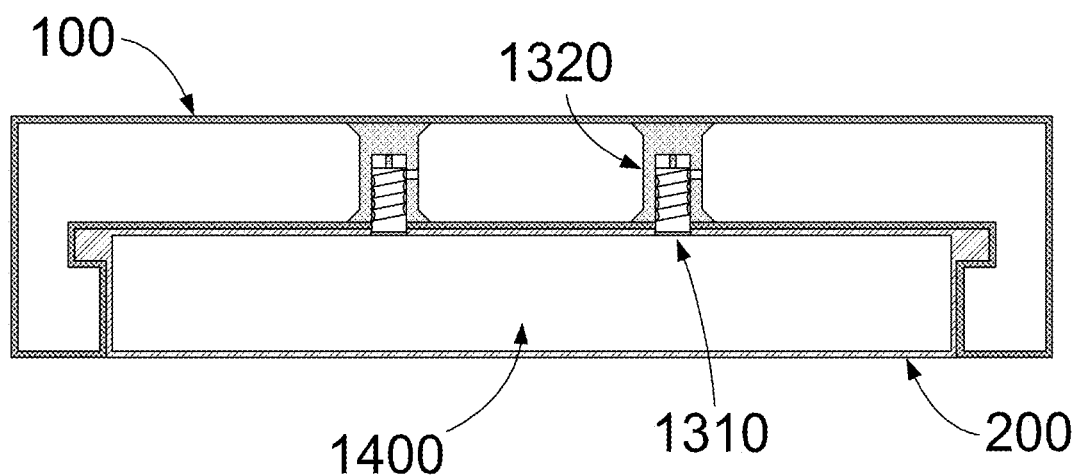

Reference is now made to FIG. 3E. FIG. 3E illustrates cross-section B-B of residual fat removal device 100. In the figure, two out of four suction ports 1310 are shown. In an exemplary embodiment of the invention, suction port 1310 is a filter that allows air suction from the cartridge 200 but prevent fat leakage from removed fat tank 1400. The suction force is created by four air pumps 1320 located in RFRD 100 on top of each suction port 1310. Additionally or alternatively, suction force is provided by reducing the air pressure in the cartridge cavity using pistons and tubes structures on the cartridge and pulling the pistons up similar to suction operation in with standard medical syringe.

RFRD 100 contains a power source (battery) and a management unit or a microprocessor, referred also as RFRD controller that manages the full treatment. After the patient is activating the residual fat removal device by pressing the start push button 1820, the management unit activates the motors to insert the needles to the skin. Needles 1230 can be inserted one at a time or all in same time. When the tip of needle 1230 reaches the fat tissue, management unit can starts the suction operation by activating pumps 1320. Suction can performed for each needle separately or for all needles together. The duration of suction is controlled by the management unit and during the suction the needle may be rotated as well as increase or decrease the penetration into the fat tissue.

Figure 3F:
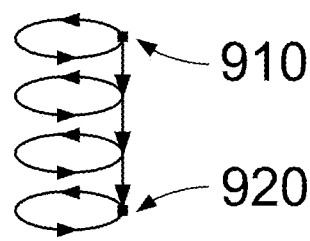
Figure 3G:
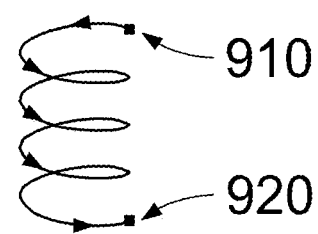

Reference is now made to FIG. 3F and FIG. 3G. In FIG. 3F and FIG. 3G two types of rotation and penetration plans are illustrated. The illustrations indicate the progress in location of the needle tip inside the fat tissue. In FIG. 3F the needle tip start at a depth and angle designated by start point 910 and make a 360 degree rotation in the same depth and then increase penetration to deeper depth in the tissue and make another 360 degree rotation. During the penetration depth increase the management unit may stop the suction operation. The needle final position is designated by point 920. In FIG. 3F the needle makes a spiral movement with combined penetration and rotation starting at position designated by start point 910 and finished at position designated by end point 920. When target depth is reached management unit power off the motor 1250 and needles are pulled back into cartridge 200. Finish indication LED 1840 is activated and the patient removes RFRD 100 from the target body organ.

As mentioned above, the exemplary embodiment of the invention illustrated in FIG. 3A-3G is an elementary system and many additional components, circuits, methods, ideas and other subsystems and many different implementations of this basic construction may be used. In the rest of the description, other embodiments are presented with additional features and subsystem. Ideas from those embodiments can be used to upgrade the above described embodiment as well as a combination of designs, circuits and idea between different embodiments is possible.

Figure 4:
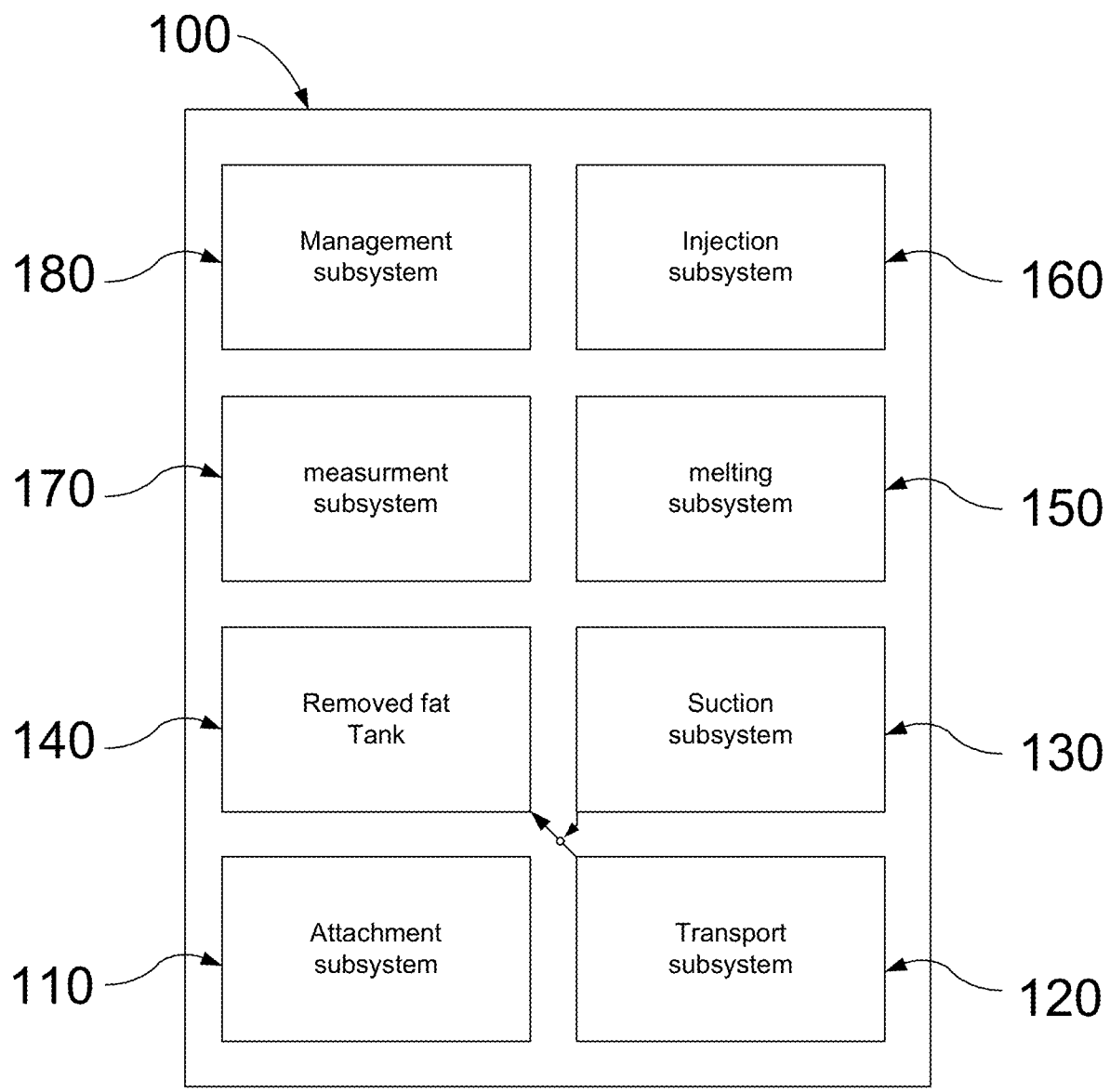
FIG. 4 is a block diagram of a more complete fat removal device, in accordance with a preferred embodiment of the invention.

Reference is now made to FIG. 4. FIG. 4 illustrates a block diagram of a more complete residual fat removal system. Residual fat removal device 100 comprises, in addition to attachment subsystem 110, transport subsystem 120, suction subsystem 130 and removed fat tank 140, as illustrated in FIG. 2 and described above, a melting subsystem 150, an injection subsystem 160, a measurement subsystem 170 and management subsystem 180.

Attachment subsystem 110 may use strips as demonstrated in the above described embodiment. RFRD may be used with different accessories where each accessory fits for different body organs. For example RFRD 100 may be fit into elastic sock that can be worn over legs and arms. Velcro strips may be used to fit RFRD to body organ. Other attachment mechanisms such as adhesive materials can be used as demonstrated below.

Transport subsystem 120 takes care for transferring the fat from the fat tissue to the removed fat tank. Basically the transport subsystem is responsible for opening a tunnel between the fat tissue and RFRD. While straight line hollow needles are the straight forward solution there are a lot of options and parameters involved in designing the transfer subsystem some example are demonstrated below. Many of the implementation as described below involved with miniaturization, micro robotics new materials and micro motors and actuator and it is likely that some of the embodiments demonstrated with the current state technologies might be improved dramatically in the near future.

Suction subsystem 130 generates the forces that drive the transit of the fats from the fat tissue to the removed fat tank 140. In the embodiment above the suction force was depended on a pressure differences and air flow. Many other physical principles may be used to force the fat to transit. Direct mechanical force on the fat can be used to force the movement of the fat in the tunnel. Surface acoustic vibration may produce similar effects. Using an electro-kinetic flow, i.e., using ionized particles and applying electric potential to push or pull the ionized particles in the tunnel is another option. When tunnels are small enough capillary forces may be used as well to move fats in the tunnels. On way valves and selective membranes are also a way to achieve suction operation in the transport subsystem. Optionally a combination of some or all of the above principles may be used.

Removed fat tank 140 is quit straight forward subsystem that need only volume large enough to occupy the removed fat. One gram of fat occupies little bit less then 1 cubic centimeter. When we talk about a 100 gram fat removal treatment a place for 90 cc is not an easy design task to achieve a friendly and commutable RFRD. One way to reduce the removed fat volume is to transform the fat to a denser material, to exhaust gases such as Oxygen, hydrogen, or $CO_2$ during the transformation chemical process as well as use the fat as a power source for the RFRD.

Melting subsystem 150 helps the suction and transport subsystem to remove the fat from the fat tissue. Melting may be done by liquefying the fats as well as breaking the fat tissue and fat cell to smaller non connected components and particles. In an exemplary embodiment of the invention, melting subsystem is implemented by direct heating of the needle tip. Additionally or alternatively, melting the fat tissue is performed by applying vibration, ultrasonic, RF, light, electric or magnetic fields and any other source of energy. The melting energy to the fat tissue can be conducted by applying the energy to the skin above the target fat tissue or, preferably, by directly transfer the energy to the target tissue. Delivering the energy to the tissue can be done using a laser and fiber optic in case a light energy is used. In case a metal needle is used in the transport subsystem, the needle can be used as an RF waveguide to direct the melting energy to the tissue. Another option is to use the metal needles as antenna array to direct the RF radiation towards the desired area.

Injection subsystem 160 is a support system that injects materials to the fat tissue or the skin tissue above it. The injection subsystem may use a separate transport subsystem or use the same transport subsystem that is used to remove the fat. The injection subsystem may be used for several functions: (1) anesthetization—inject anesthetizing materials to reduce the discomfort and pain of the fat removal, (2) Injection of melting materials before the fat removal, (3) injection of materials to release fats from the fat cells, (4) injection of filling and/or healing materials to the tissue after the fat removal, and (5) supplementary drug delivery.

Measurement subsystem 170 is a support subsystem that helps in control of the fat removal treatment. The following measurements are desired for residual fat removal devices: (1) amount of fat removed, (2) thickness of the skin tissue and the fat tissue in the target body organ, and (3) Any obstacles such as blood vessels that need to be avoided (or targeted) by the transport system. Measurements of the skin and fat tissue thickness may be practically and inexpensive done using common ultrasound echo measurements techniques. In tissue measurement can be done using standard miniaturized cameras which are commodity today.

Management subsystem 180 is the heart of a residual fat removal system. A simple residual fat removal system may be implemented with a simple non central control scheme, however, to integrate many of the techniques introduced in the invention and to efficiently time all subsystem a central management subsystem is essential. The management system is preferably implemented using an embedded micro controller that commands and activates all functions and activities of the other subsystem. Management subsystem 180 needs to provide communication infrastructure with all other controllable or reporting subsystem and component. To implement such infrastructure several media can be used. Medium can include already used for different function medium such a power lines, fiber optics or metal tubes or structure. In some case wireless communication is the easiest way to carry the communication over the RFRD. Management subsystem 180 provides communication with the user (the patient). The management subsystem gets patient instructions and provides patients with status. In addition, management subsystem provides to the user additional services such as alarming and reminders of future treatments, reminder for the target organs treatment plan, historical data retrieval and statistics, etc.

In the following embodiments of the invention we revisit the fat removal process with in depth view of the implication to the fat tissue to provide alternative methods and improvements to the residual fat removal.

Fat tissue is composed mostly from fat cells and roughly 80% of the tissue is fat in the form of triglyceride droplets in the fat cells. However, one should remember that in addition to fat stored as triglyceride molecules in the fat cells, there are in the tissue other components such as the cells structure (membrane and nucleus and other cell organs and proteins) as well as other factors such as blood vassals, nerves axons and other fat tissue structural (non fat) cells. It is highly desire that those other cells and organs will stay intact or at least will suffer a recoverable damage. The simplest way to approach that is to use as thinnest as possible needles. However, the smaller the needles are it is harder to transfer the fat from the tissue to the RFRD and larger suction force, more time and more needles are needed to transfer the fat. If the inner diameter of the needle is less then the fat cell diameter (<0.2 mm), fat cells structure must be broken or melted before the suction operation.

Needles with inner diameters less then 0.2 mm referred hereafter as "micro needles". In an exemplary embodiment of the invention, residual fat removal device is comprises from array of micro needles. To compensate the reduction in suction capacity, more needles are used.

Figure 5A:
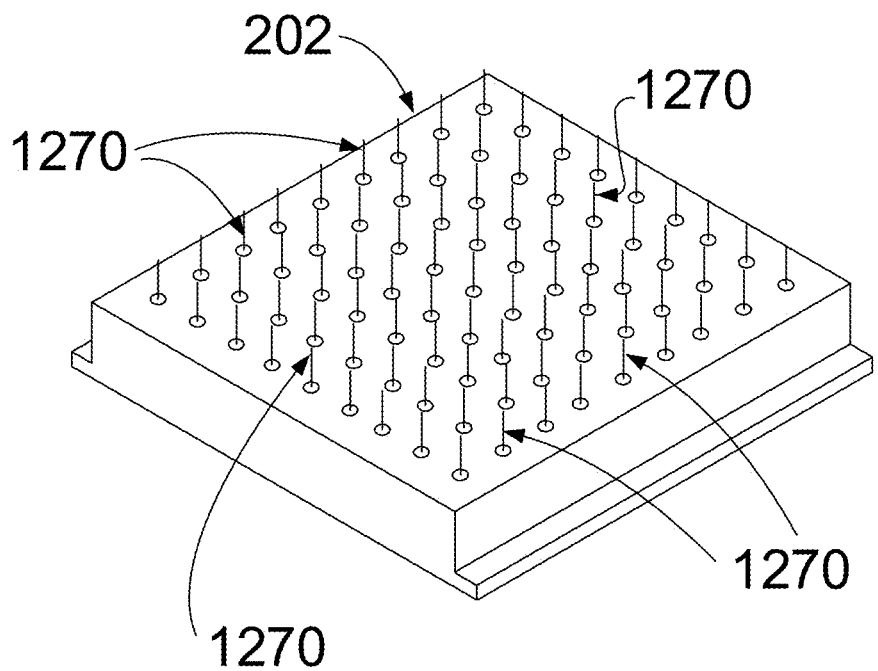
FIGS. 5A-5D are illustrations of embodiment of a version of fat removal device incorporating micro needles in accordance with a preferred embodiment of the invention.
Figure 5B:
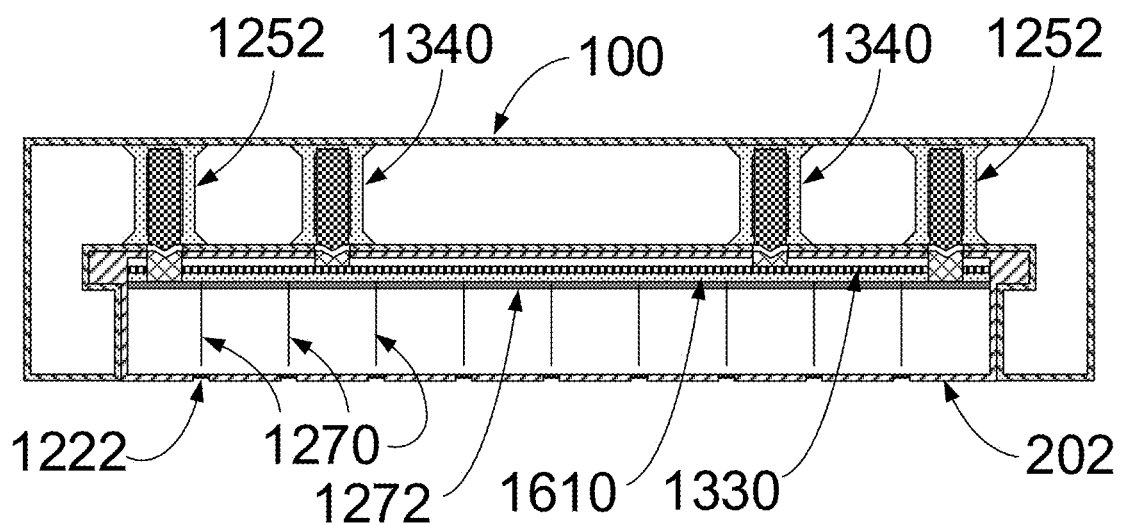

Reference is now made to FIG. 5A. FIG. 5A illustrates an isometric bottom view of disposable cartridge 202. Disposable cartridge 202 is inserted to a residual fat removal device similar to the one illustrated in FIG. 3. In the figure the needles state is maximum penetration state. Disposable cartridge 202 comprises array of micro needles 1270. Cross-section of disposable cartridge 202 is illustrated in FIG. 5B. Reference is now made to FIG. 5B. In this figure cartridge 202 is in the initial state, i.e., before use, and micro needles 1270 are packed inside cartridge 202. Micro needles 1270 are nailed to a needle plate 1272. Needle plate 1272 is used as a piston inside cartridge 202 cavity. Needle plate 1272 is moved up and down by needle plate motors 1252 that reside in residual fat removal device 100. Two such motors are shown in FIG. 5B, however, other embodiment can used one or more then two such motors. Reference is now made to FIG. 5B. FIG. 5B illustrates a cross-section view of cartridge 202. Cartridge 202 comprises a suction piston 1330 reside on top of needle plate 1272. Suction piston 1330 is moved up and down by a Suction piston motors 1340 reside in the residual fat removal device 100. Two such suction piston motors 1340 are shown in the cross-section of FIG. 3B, however other embodiment can use one or more then two such motors. An injection material 1610 resides in between needle plate 1272 and suction piston 1330.

Figure 5C:
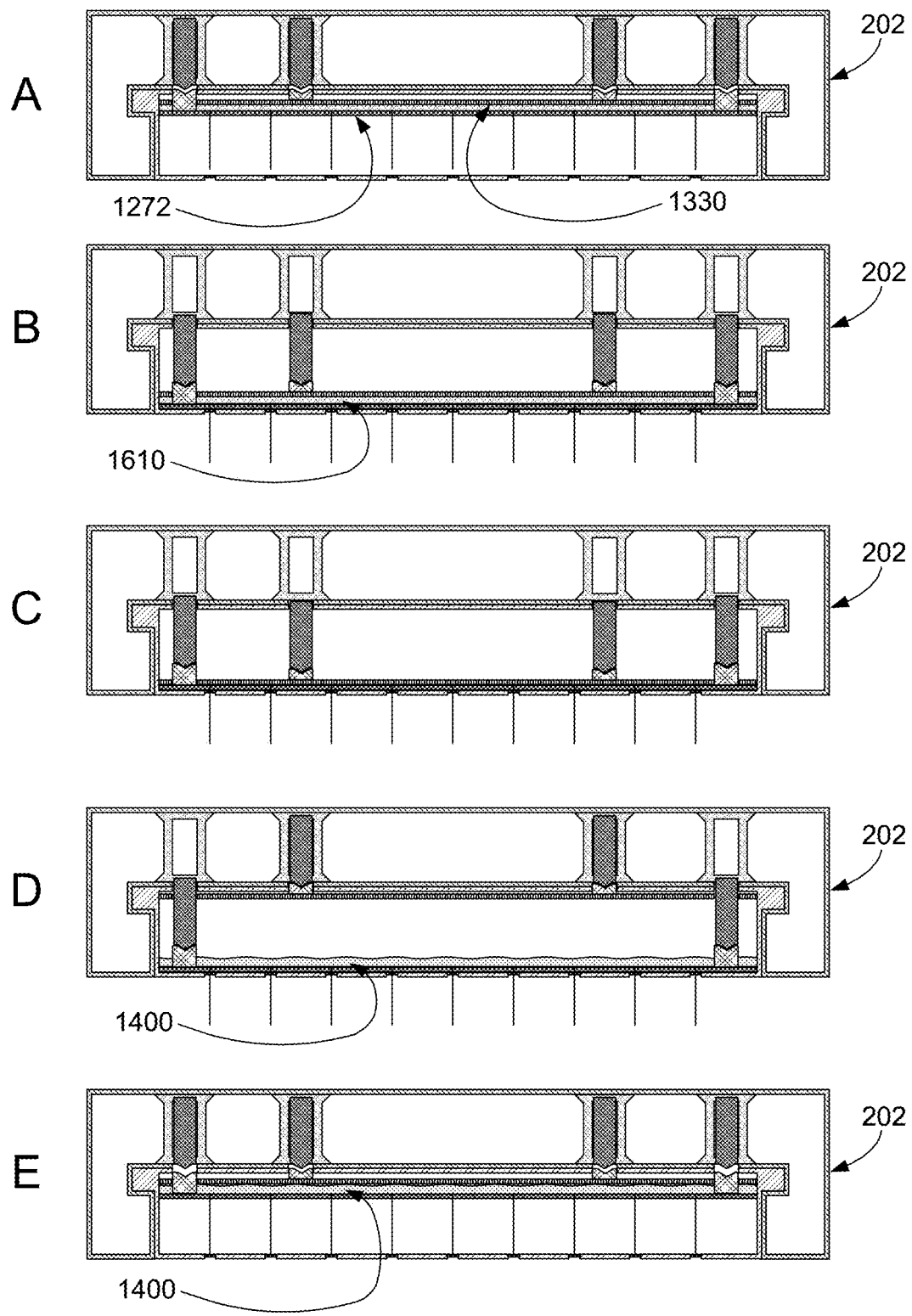
Figure 5D:
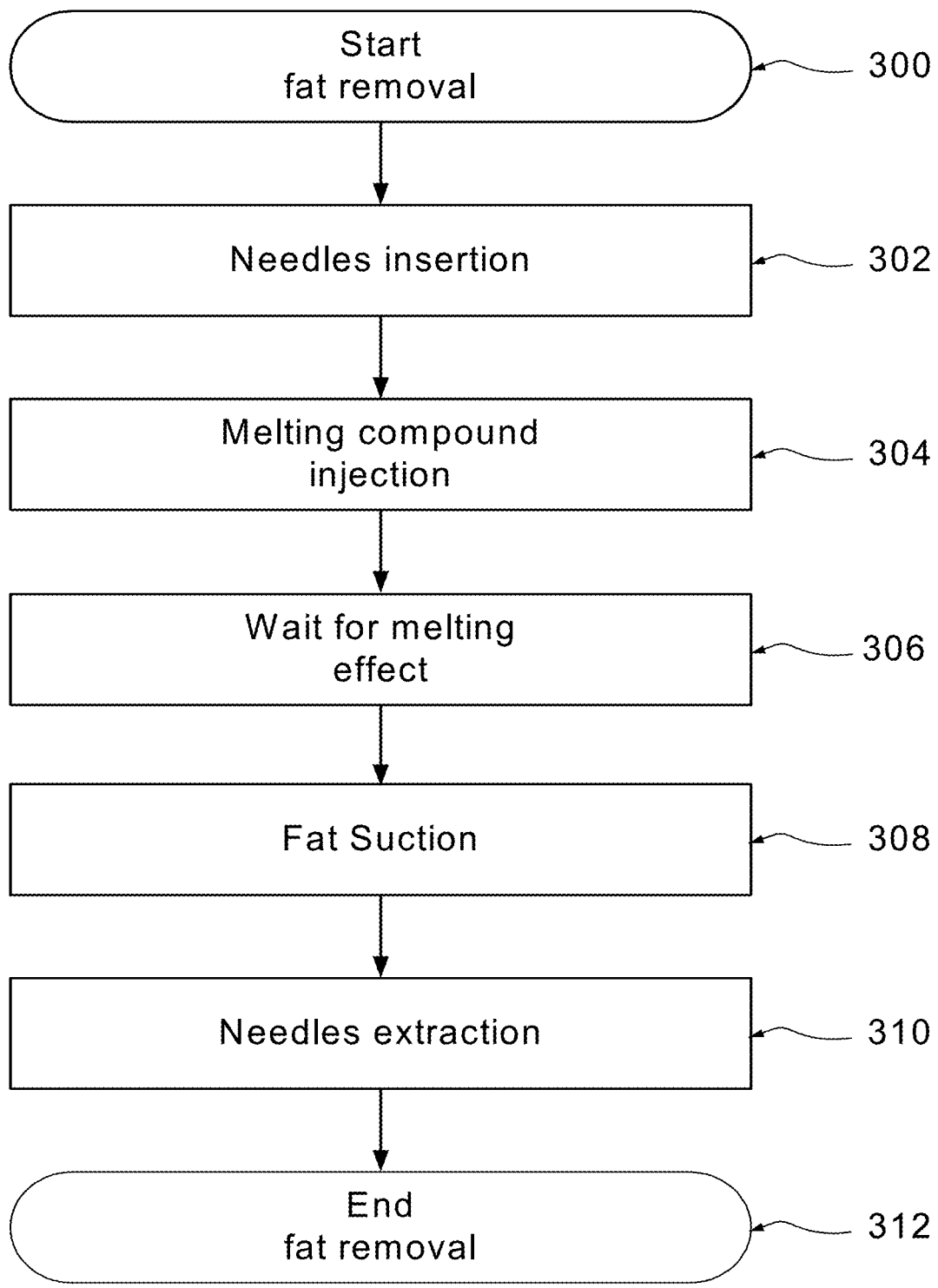

Reference is now made to FIG. 5C and FIG. 5D. FIG. 5C illustrates the dynamic state varying of residual fat removal device 100 and disposable cartridge 202 during the different stage of the fat removal. FIG. 5D illustrates the flowchart of the fat removal process in accordance with those states illustrated in FIG. 5C. The flowchart of FIG. 5D is a detailed description of stage 40 of FIG. 1. When residual fat removal starts, stage 300, cartridge 202 is in state A of FIG. 5C. RFRD is performing needle insertion stage 302 by pushing down both needle plate 1272 and suction piston 1330. Micro needles 1270 are very thin so patient should not feel any pain. In order to reduce the risk of pain further a control on the speed of penetration is possibly applied. When the needles reached to the target depth (the fat tissue) treatment plan moves to melting compound injection stage 304. In this stage, the injection materials, containing the melting compound, is injected to the fat tissue.

State B of FIG. 5D shows the state of the needle plate 1272 and suction piston 1330 just before injection starts and where the needle reaches its maximum depth. Injection may starts before the needles reach the maximum depth and can be done simultaneously with needles penetration.

State C of FIG. 5C shows the cartridge 202 when injection had been finished and needles are in maximum depth state. When the target depth has been reached, RFRD moves to injection stage 304. Injection is performed by closing the gap between needle plate 1272 and suction piston 1330. Injection materials 1610 are forced to exit through micro needle 1270 in to the fat tissue. Injection materials 1610 contain a melting compound that destroy the fat cell membrane and pour triglycerides droplets to the intercellular fluid. This process may take a while so RFRD moves to stage 306 and wait until the melting process is effective.

Next, RFRD moves to stage 308 to perform the fat suction. Fat suction is performed by increasing the gap between needle plate 1272 and suction piston 1330. This operation creates vacuum that sucks up the inter-cellular fluids surrounding needles tip. Additionally or alternatively, suction pump may be used. The removed fat 1400 is exiting through the hole in the top side of the needles and accumulated in disposable cartridge 202 cavity as illustrated in state D of FIG. 5C. The duration of suction is depended on the number of needle, needles diameters as well as other parameters.

When suction duration met, RFRD moves to needle extraction stage 310. In this stage, needle plate 1272 is pulled up until the needles are back inside the cartridge. The removed fat 1400 are still reside between needle plate 1272 and suction piston 1330 as illustrated in state E in FIG. 5C. In this stage, RFRD finish the fat removal stage 312. RFRD assert treatment end indication and patient can detach the RFRD and dispose cartridge 202 as illustrated in stage 50 in FIG. 1.

As mentioned before melting the fat tissue is very important factor as needle inner diameter gets smaller. In the following embodiment, additionally or alternatively, melting subsystem comprises an electrical melting subsystem.

Reference is now made to FIG. 6. FIG. 6 illustrates an embodiment that implement an electric melting system. In the figure top view of needle plate 1272 is shown. The top of the needle plate 1272 comprises a PCB 1372. Needles 1270 are assembled on PCB 1372. Each needle 1270 has a trace 1374 to a signal generator semiconductor chip 1376 that is assembled on PCB 1372 (only some exemplary traces are shown in the figure). A connector 1378 on PCB 1372 is assembled to communicate with RFRD controller. Additionally or alternatively, RFRD controller includes a signal generator to excite the needles independently. Signal generator may provide DC voltage, AC voltage or RF signals to needles 1272. When RF signals are injected, the needle array act as antenna array and by controlling the amplitude and phase for each needle a directed beam of energy can be formed. RFRD may use such electrical exciting to transfer energy to the fat tissue and to improve the fluidity of the fat.

Micro needles may be manufactured like a standard needle from stainless steel; however, when thickness is reduced it is more likely to use new emerging technologies such as nanotechnologies techniques to implement the transport subsystem as well as other parts of the system. In an exemplary embodiment of the invention, needles are implemented on semiconductor die or chip. Additionally or alternatively, needles are carbon nanotubes.

In an exemplary embodiment of the invention, when not inserted to the skin needles are folded in initial state. Folded needle is implemented in nano technology techniques. Reference now is made to FIG. 7. FIG. 7 illustrates two types of folded structures of micro needles implemented in MEMS technology on semiconductor chip. FIG. 7A illustrates side view cross-section of telescopic needle in folded state and FIG. 7B illustrates the same needle embodiment when the needle is in open state. FIG. 7C and FIG. 7D illustrate alternative spiral folded needle embodiment. In FIG. 7C a top view of the needle structure in folded state is shown and in FIG. 7D a side view cross-section of the needle structure in open state is shown. Both embodiments implemented on a silicon semiconductor substrate 1274 (only small part of the full chip substrate is shown). Both embodiments use MEMS technology movable actuator 1276. Actuators 1276 are moved between needle close and needle open positions when an electric voltage applied to them. In the telescopic embodiment four silicon rings 1278 are sculptured over substrate 1274. Those rings are formed by standard semiconductor manufacturing process. The external ring 1278 is fixed and attached to substrate 1274. The other internal rings 1278 have each actuator 1276 attach to it and the actuator slides over the adjacent ring 1278. To open the needle, actuators 1276 are sliding up to the open position each actuator 1276 pushes the ring it is attached to upwards. The final open state is illustrated in FIG. 7B. Using a semiconductor manufacturing processes enables production of very thin needles with micrometers resolutions. The number of rings in the figure, four, was chosen for illustrative purposes only. In an exemplary embodiment of the invention, two or more rings may be used. The penetration of this needle in the skin may be controlled either by partial activation (sliding) of all actuators 1276 together or by activating only part of the actuators 1276.

Reference is now made to the second folded needle embodiment illustrated in FIG. 7C and FIG. 7D. In the figures, a micro needle 1280 is attached to chip substrate 1274 and spirally folded over the substrate from outside in. the tip of the needle is folded upwards and located in the center of the spiral. Micro needle 1280 is placed on a specific area on the substrate limited by four silicon fences 1282. When needle 1280 is in folded state only a small tip is stand out. Opening the needle is performed by activating MEMS actuators 1276 attached to each fence 1282. Fences 1282 pushes the external parts of the spiral inwards and in turn pushes the needle tip upwards. When the fences reach their open position the needle is almost straight as illustrated in FIG. 7D. Micro needle 1280 may be made from variety of materials including carbon nanotubes. Additionally or alternatively, applying an electronic voltage to needle 1280 reduce its flexibility and encourage standing up of needle 1280.

Figure 12A:
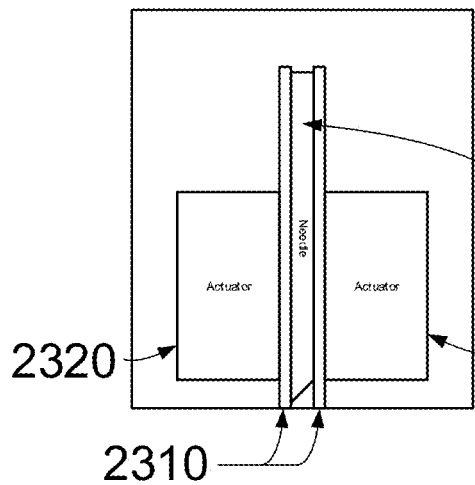
FIGS. 12A-12D are illustrations of exemplary embodiment of an alternative versions of micro needles for the fat removal device, in accordance with a preferred embodiment of the invention.
Figure 12B:
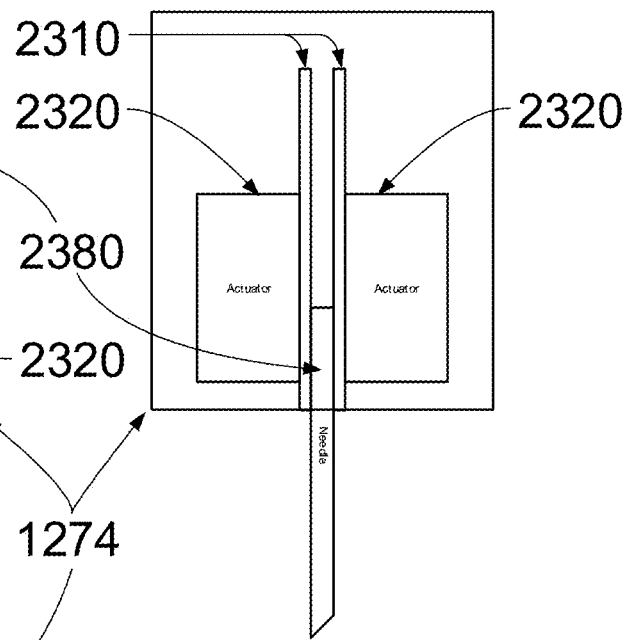
Figure 12C:
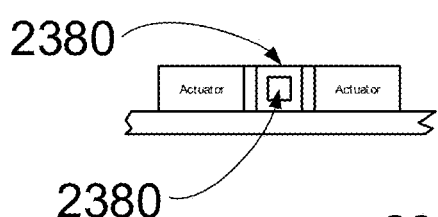

Additionally or alternatively, in a preferred embodiment of the invention the micro needles are implemented in the plane of the semiconductor substrate. Reference is now made to in plane folded needle embodiment illustrated in FIGS. 12A to 12D. In FIG. 12A a semiconductor substrate 1274 is used to fabricate in plane hollow needle 2380. Using well known masking and itching MEMS fabrication processes, needle 2380 is not attached to substrate 1274 so it is free to slide over substrate 1274. The tip of needle 2380 is formed with sharp edges to ease the penetration to the skin. To guide and control the movement of needle 2380, needle 2380 is surrounded by movement control and force transmission subsystem 2310. Adjacent to movement control and force transmission subsystem 2310 actuators 2320 are located. Actuators 2320 generate the forces to move needle 2380 so it will penetrate into the skin. Movement control and force transmission subsystem 2310 transfer actuators 2320 force to the needle and guide the needle in the right direction. FIG. 12B illustrates needle 2380 relative to substrate 1274 in full open position. FIG. 12C illustrates side view of the die. In the figure the needle 2380 hollow cavity 2382 is visible. There are many alterative ways to implement both actuators 2320 and movement control and force transmission subsystem 2310.

Figure 12D:
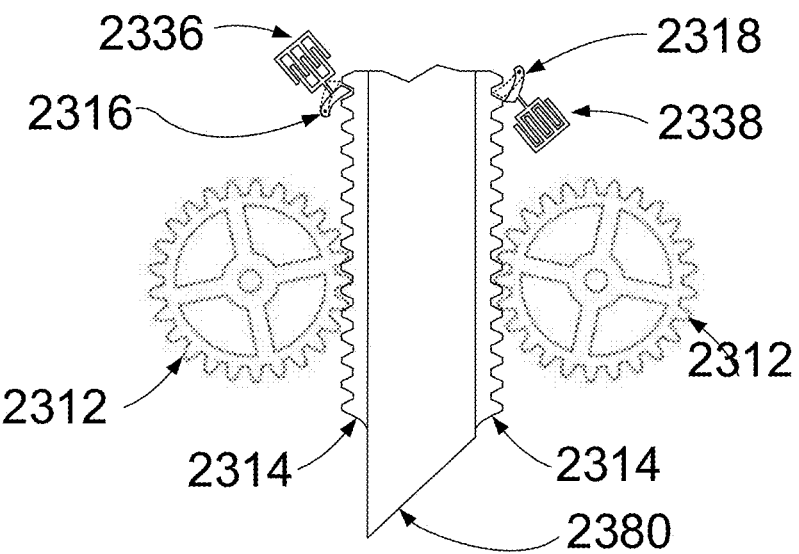

Reference is now made to FIG. 12D. FIG. 12D illustrates a simplified embodiment of movement control and force transmission subsystem 2310. Teeth bars 2314 are attached to the sides of needle 2380. The linear movement of the needle is generated by the rotation of teeth wheels 2312. Rotating a teeth wheel on MEMS is well known in the art and many actuators and MEMS engines architectures can convert multiple cycles of actuation to rotation. Alternatively, actuators can directly drive teeth bars 2314 for example by one tooth displacement in each actuation step. Optionally, transmission gears can be inserted to adapt the actuator power to the force that is needed to penetrate the skin. The speed of penetration is controllable and is used to minimize and even eliminate penetration pain.

Optionally, a ratchet mechanism can be added to movement control and force transmission subsystem 2310. One way ratchet that ensure no backwards movement during penetration or withdrawal of the needle can be used. Alternatively, two way ratchet can be used. In FIG. 12D a controllable two way ratchet is implemented. A ratchet tooth 2316 prevents penetration movement and a ratchet tooth 2318 prevents withdrawal movement. Both ratchet teeth 2316 and 2318 can be active or inactive. In the figure ratchet tooth 2316 is active and ratchet tooth 2318 is inactive so the needle in this case can not penetrate but can withdraw. Actuators 2336 control ratchet tooth 2316 and actuators 2338 control ratchet tooth 2318. Actuators 2336 and 2338 push the teeth to activate the ratchet operation and pull the ratchet teeth to deactivate the ratchet.

In FIGS. 7 and 12 a demonstration of implementing micro needles on a semiconductor substrate was shown, however such an implementation open the door for integration of other subsystem of residual fat removal device in to the same integrated circuit semiconductor die. In an exemplary embodiment of the invention, a single semiconductor die is used to integrate a transport subsystem (array of micro needles). Additionally or alternatively, the die comprises management subsystem. Additionally or alternatively, the die comprises measurement subsystem. Additionally or alternatively, the die comprises melting subsystem. Additionally or alternatively, the die comprises suction subsystem. Additionally or alternatively, the die comprises injection subsystem. Additionally or alternatively, the die comprises attachment subsystem. Additionally or alternatively, the die comprises hollows regions that can be used for the removed fat tank and/or melting materials and/or injection materials.

In an exemplary embodiment of the invention, the integrated die is based on semiconductor materials such as silicone, germanium, carbon, plastic, organic materials and variety of polymers or a combination of them on a single die.

Figure 8A:
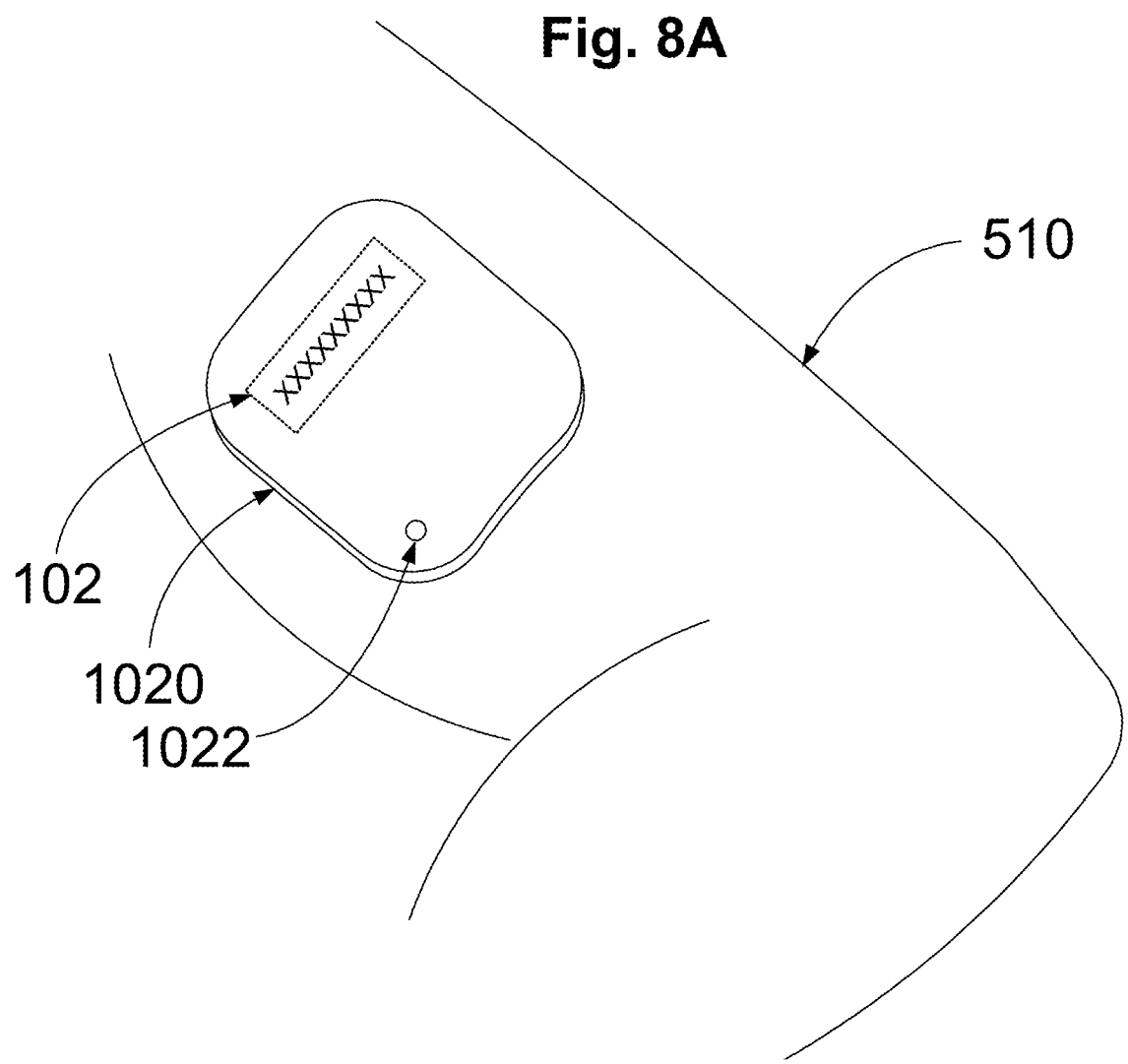
FIGS. 8A-8C are illustrations of exemplary embodiment of a patch shape version of fat removal device incorporating folded micro needles in accordance with a preferred embodiment of the invention.
Figure 8B:
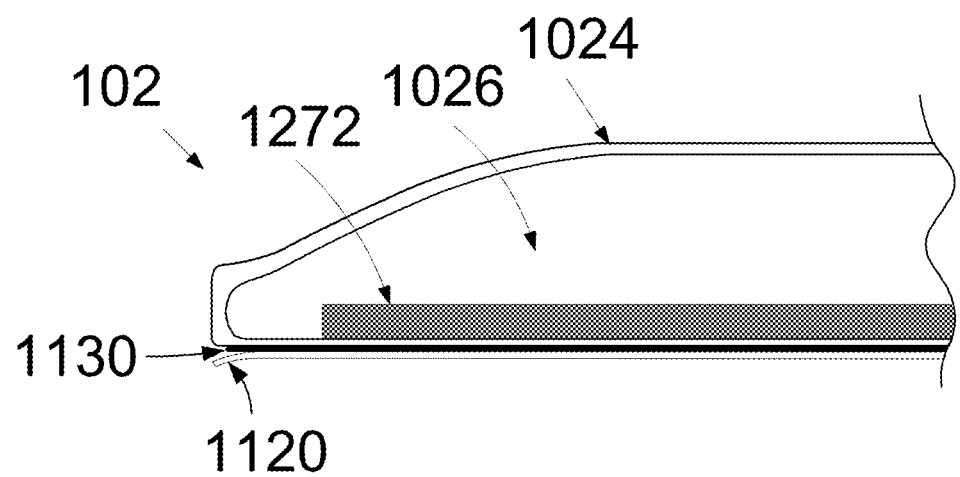
Figure 8C:
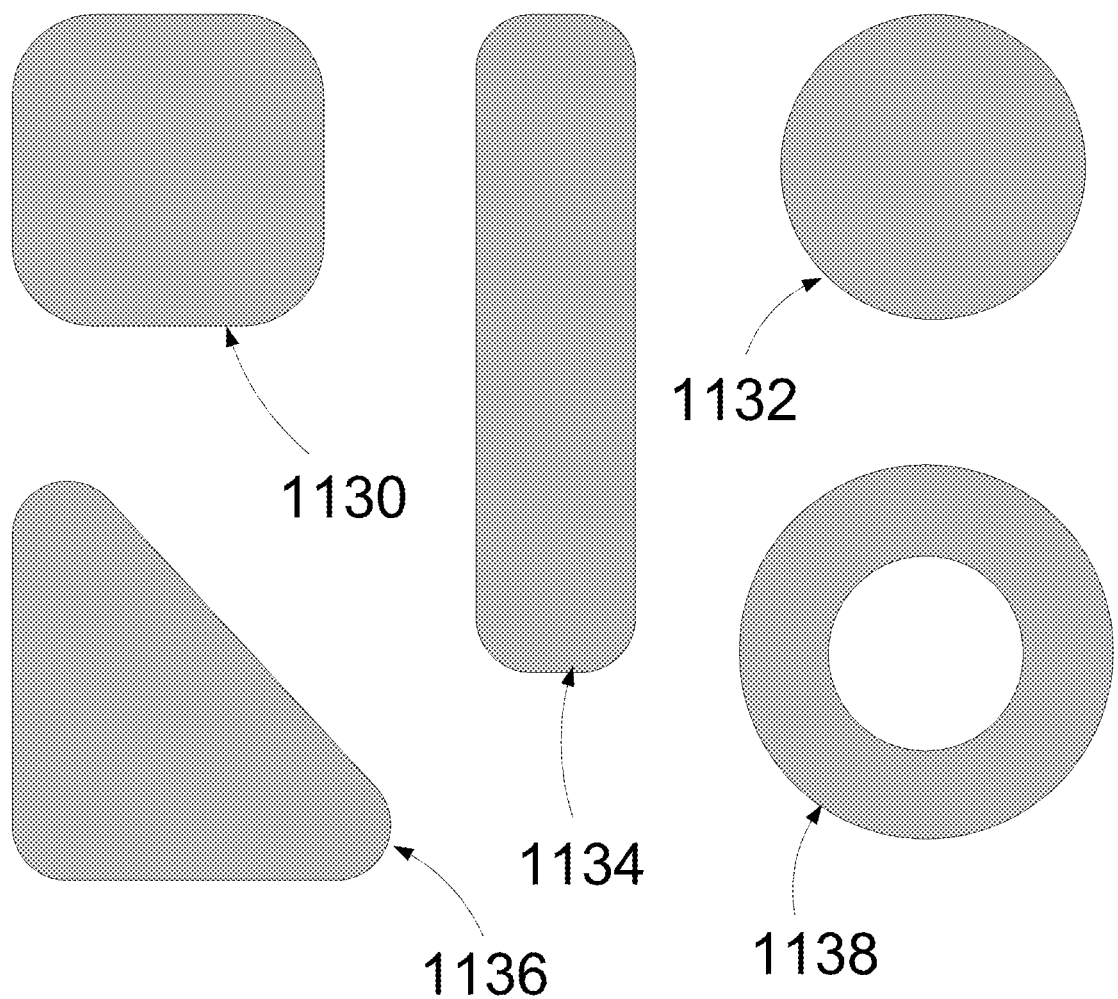

Reference now is made to FIG. 8. FIG. 8 illustrates a preferred embodiment of the invention using a semiconductor die with folded needles. FIG. 8a illustrates an exemplary patch shape residual fat removal device. Residual fat removal device 102 is a flexible adhesive patch. The figure illustrates RFRD patch 102 stuck on patient's arm 510. Residual fat removal device 102 contains a label 1020 that describe the type of the RFRD patch 102. Patches are classified by variety of features. In an exemplary embodiment of the invention, patches are classified by their size and shape (see FIG. 8C). Additionally or alternatively, RFRD patches 102 are classified by the amount of fat they designed to remove. Additionally or alternatively, RFRD patches 102 are classified by the type of body target organ they are fitted to. Additionally or alternatively, RFRD patches 102 are classified by the maximum depth from skin surface they suck fat from. Additionally or alternatively, RFRD patches 102 are classified by the type of fat suction. For example, fat suction type can be in the form of complete fat cell suction or just fatty acid suction without destroying complete fat cells (see a discussion on this feature later in the invention description). Additionally or alternatively, RFRD patches 102 are classified by the existing and the amount of anesthetization. Additionally or alternatively, RFRD patches 102 are classified by the additional drug they deliver to the body in the treatment.

Optionally, RFRD patch 102 has an indicator 1022 that indicate when treatment is finished and the RFRD patch is no longer valid and should be disposed. In this embodiment treatment is preferably started automatically as soon as the RFRD patch 102 is sensing that the protective sheet is removed (see FIG. 8B) and it is in full contact with the patient's skin. FIG. 8B illustrates cross-section view of the left side of RFRD patch 102. RFRD patch 102 has a bottom protective sheet 1120 protecting an adhesive layer 1130 that attach the RFRD patch 102 to patient's skin. Protective sheet 1120 is removed before the patient start the treatment. RFRD patch 102 comprises a die 1272 that contains folded needles as well all integrate other RFRD subsystem. RFRD patch 102 protected by a thin protective case 1024. A spare volume 1026 in the protective case 1024 is used for additional RFRD subsystems such as other semiconductor dies that might be needed in the system, a battery, injecting materials tanks as well as the removed fat tank.

Reference is now made to FIG. 8C. FIG. 8C illustrates some preferred shapes of the RFRD patch embodiments. Squared shape 1030 and circle shape 1032 are the best shapes to be used when target body organ is large relative to patch area. In some cases rectangle/strip shape 1034 are better choice. In other cases a more complex shape like triangle 1036 or ring 1038 (for example for areas around the nipples and belly button) are recommended. For a specific target body organ patch may also be non-flat and curved to match approximately the target body organ three-dimensional shape.

Although previous embodiments with array of micro needles are generating less damage to the tissue due to the small diameters of the needles, an alternative embodiment that penetrates the skin tissues (the epidermis and the dermis) in one place similar to a fat removal surgery is described below. In the same way as a standard liposuction, the aim of this embodiment is to perform the fat removal in areas in the fat tissue that are not directly under the skin penetration point but horizontally apart from penetration point up to about 10 cm. To cover such area, the residual fat removal device must turns from vertical penetration in the skin tissues to horizontal penetration in the fat tissue. To accomplish that penetration opening need to be larger the simple needle diameter to enable the use of more sophisticated transport subsystem. However, such a system may still be thin due to current and emerging miniaturization technologies. In the following example we will demonstrate an embodiment of the invention that uses miniaturization and micro or nano robotics technologies to implement a residual fat removal device.

Figure 9A:
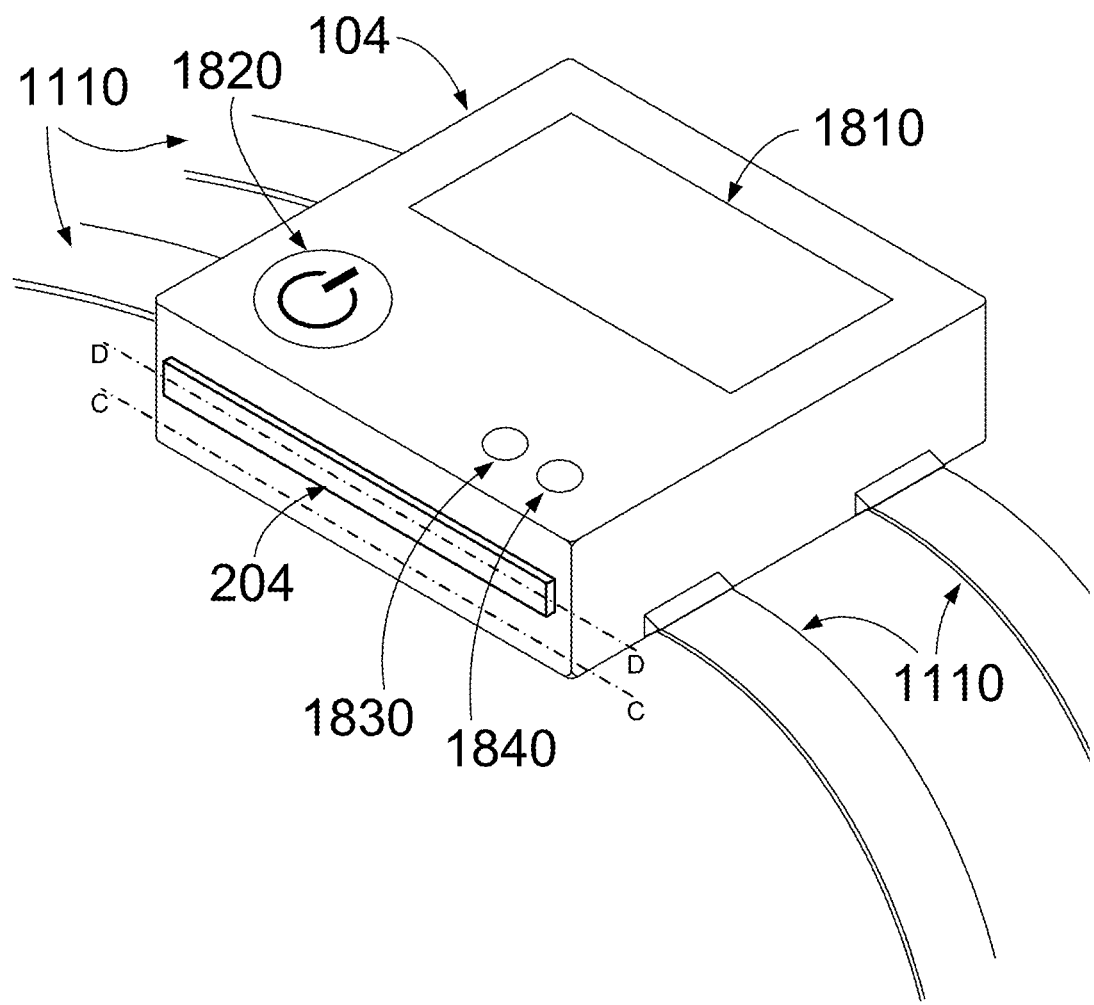
FIGS. 9A-9H are illustrations of exemplary embodiment of a worm shape transport subsystem version of fat removal device in accordance with a preferred embodiment of the invention.
Figure 9B:
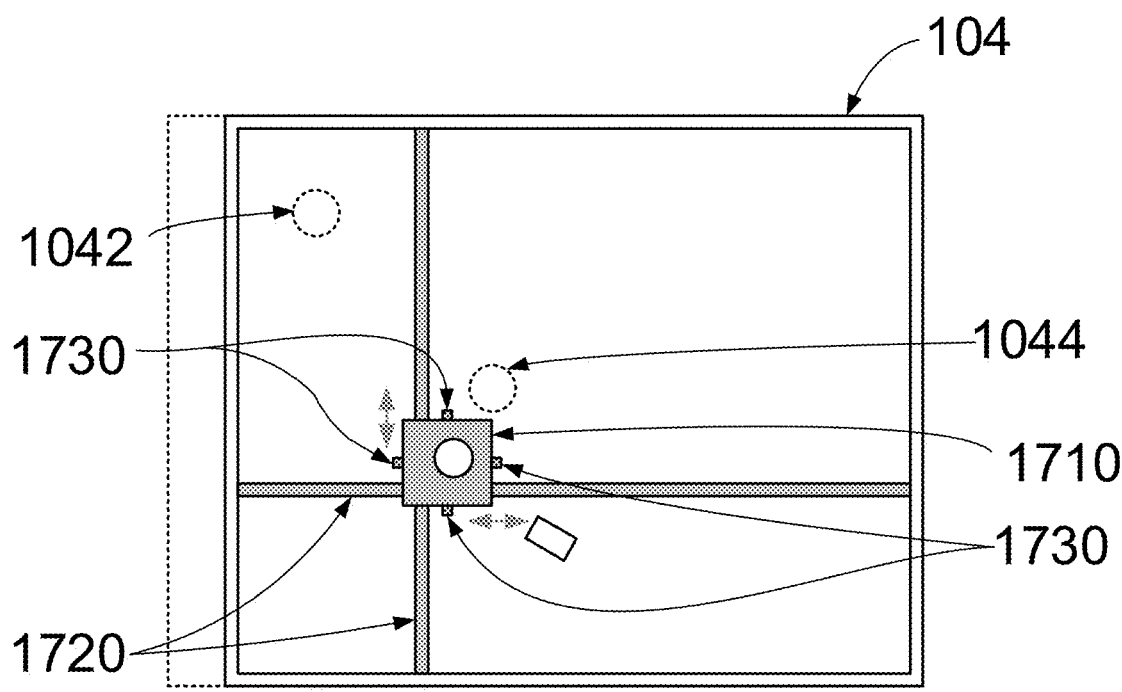
Figure 9C:
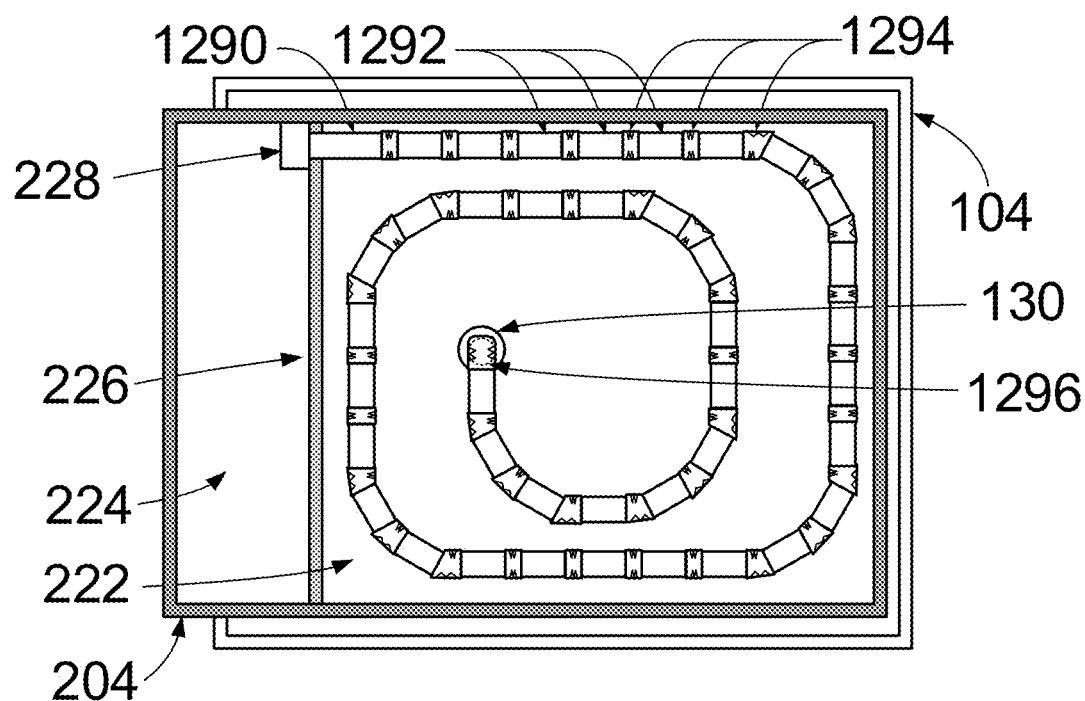

Reference now is made to FIG. 9A-FIG. 9H that illustrate a micro robotic RFRD using a single penetration opening in the skin. In an exemplary embodiment of the invention illustrated in FIG. 9A, Residual fat removal device 104 comprises a disposable cartridge 204 and strips 1100 to attach RFRD 104 to the target body organ. RFRD 104 has a start push button 1820 to start fat removal operation and two indication LEDs 1830 and 1840 to indicate RFRD 104 is in operation and finished respectively. In addition, RFRD 104 has a display 1810 to provide additional information to the patient. Two cross-section lines C-C and D-D are shown in the figure. Cross-section C-C is shown in FIG. 9B. Cross-section D-D, is shown in FIG. 9C.

Reference is now made to FIG. 9B. FIG. 9B illustrates the bottom inside of RFRD 104. Bottom inside of RFRD 104 contains a scanning head 1710. Head 1710 can reach any point in the bottom surface of RFRD 104 by sliding over spiral rods 1720. Head 1710 contains four ultrasound transducers 1730 that are used to map the body tissues located under RFRD 104. At the beginning of the treatment RFRD controller instructs the scanning head 1710 to scan all the area of the skin under RFRD 104. Using the ultrasound echoes, received by the ultrasound transducers 1730, a 3D map of the skin and fat tissues is created. The map contains the thickness of the dermis, epidermis and the fat tissue in each location, as well as objects to be avoided such as blood vessels, nerve sensors, etc. based on this information RFRD controller plan the full path of suction in the tissues (as will be describe in more details better later). In specific, RFRD controller decides on the skin penetration point 1042. To start the suction, RFRD controller need to insert the transport subsystem into the body. The transport subsystem is made from a short cannula and a worm-like device illustrated in FIG. 9C.

Figure 9D:
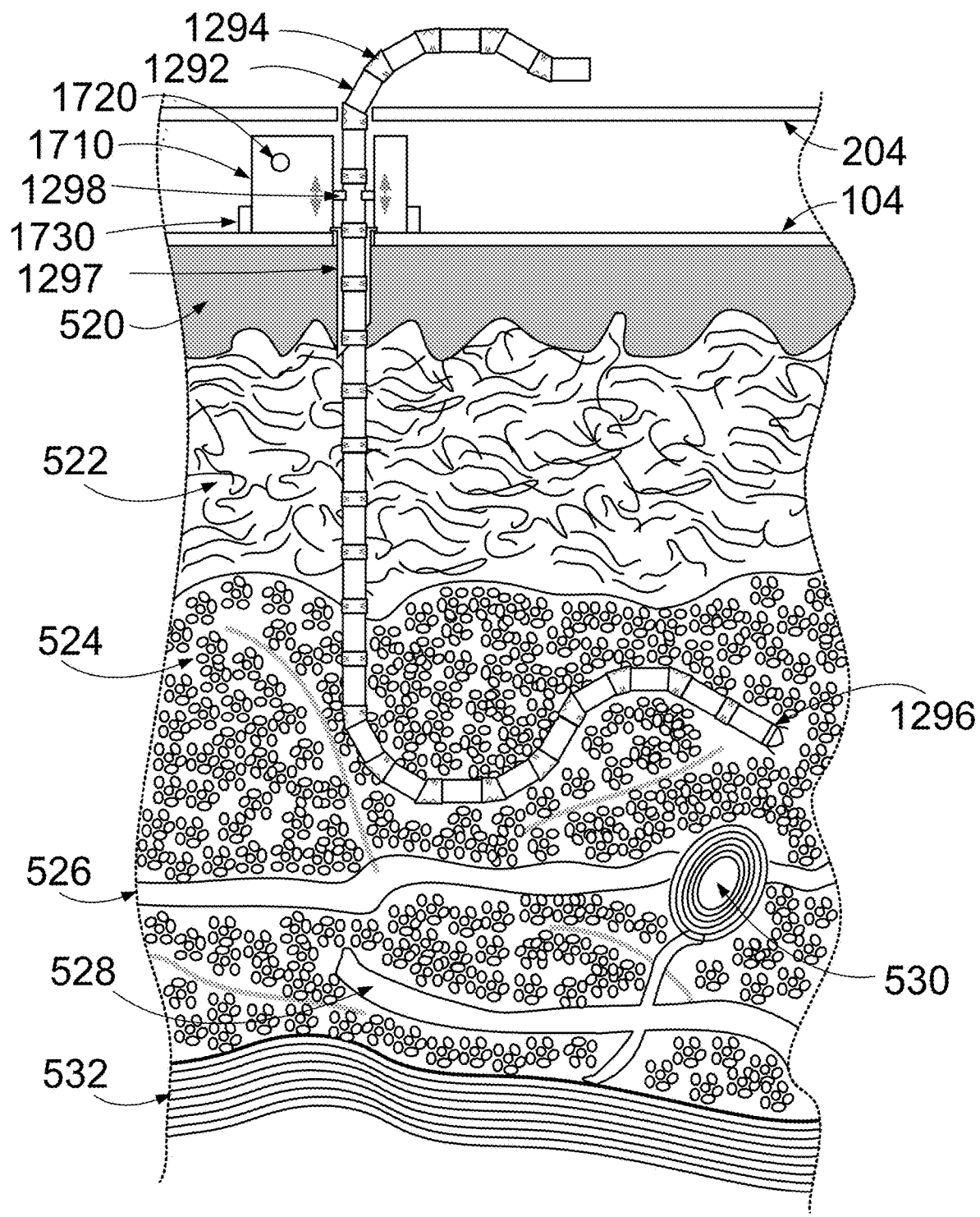
Figure 9E:
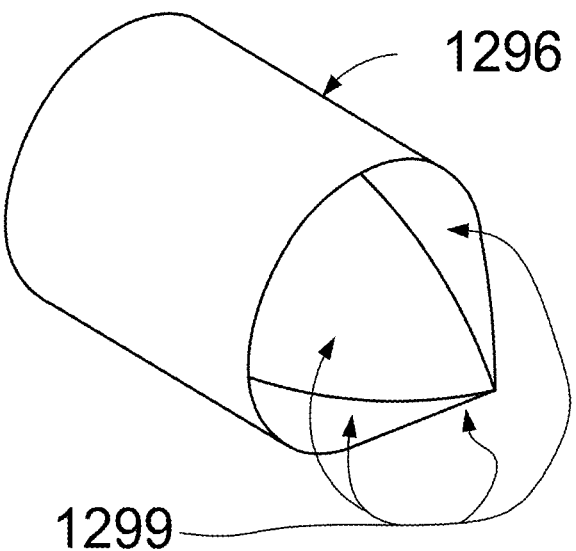
Figure 9F:
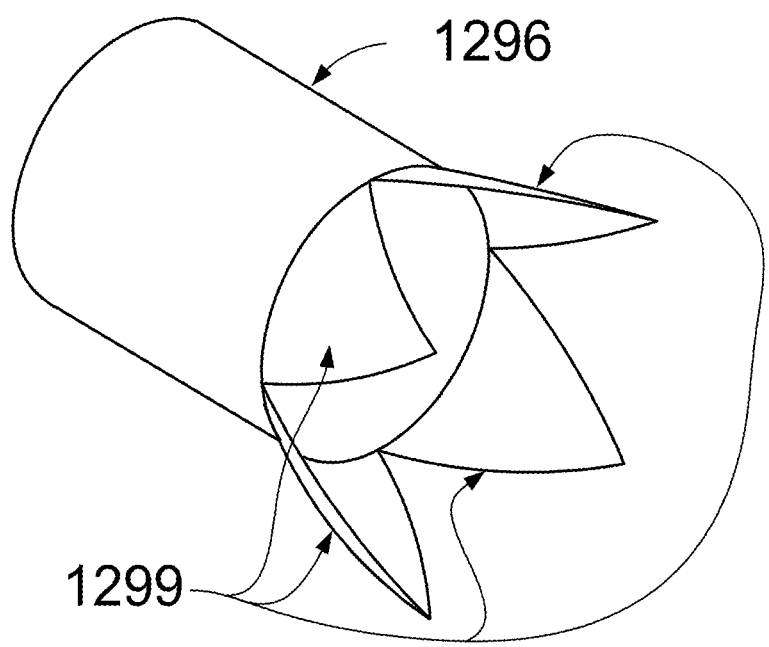
Figure 9G:
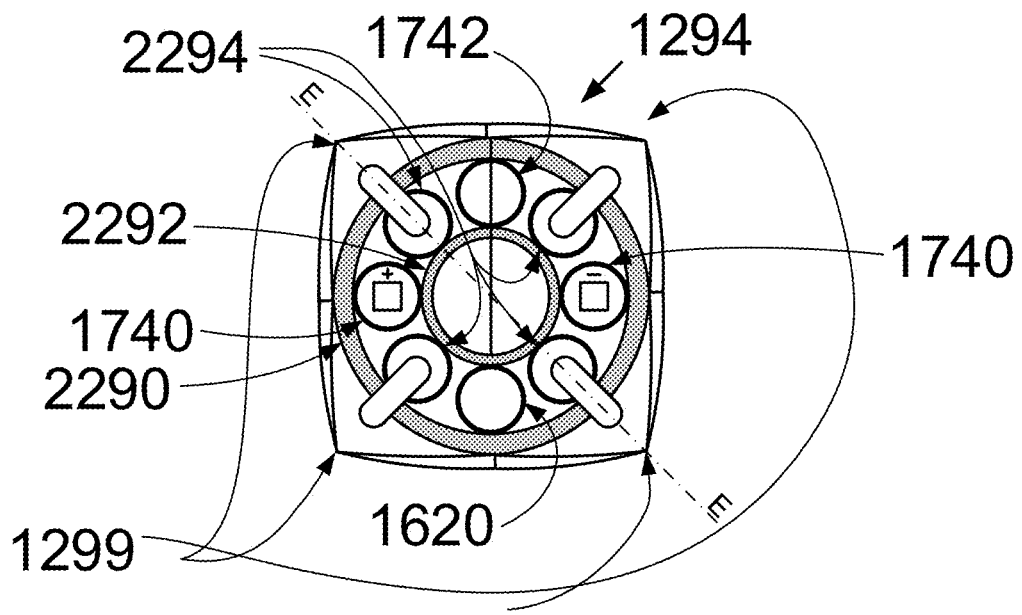

Reference is now made to FIG. 9C. FIG. 9C illustrates the inside of disposable cartridge 204. In FIG. 9C, disposable cartridge 204 is inserted in RFRD 104. Cartridge 204 is divided to two chambers: (1) worm chamber 222 and (2) materials chamber 224. The chambers are separated by a sealed partition 226. Materials chamber 224 is used for the removed fat tank as well as, optionally, other materials that are injected during the treatment. Worm chamber 222 contains a folded worm-like transport subsystem comprising: (1) worm tail 1290 (2) multiple worm elements 1292 (3) multiple worm connection elements 1294 and (4) worm head 1296. Worm tail 1290 is stationary and attached to a connector 228. Connector 228 provides all inputs and outputs ports from and to the worm. Ports are both for materials that flows in or out of materials chamber 224 as well as power lines, fiber optics cables, electronic signals for command measurements and statuses that are coming from or going to RFRD 104. Worm elements 1292 are rigid cylindrical parts illustrated in details in FIG. 9G. Worm connection elements 1294 give the worm its mobile abilities. Each worm connection element 1294 is able to bend in two dimensions allowing the overall worm to crawl in three dimensions from the cartridge to the fat tissue and inside the fat tissue as illustrated in FIG. 9D. Each worm connection element has its own serial number (i.e., ID) and RFRD controller is able to control each element separately. By simultaneously controlling all connection elements 1294 RFRD controller determine the movement of the worm. Worm head 1296 initially located in a passage 1044 between cartridge 204 and device 104. Worm head 1296 details are illustrated in FIG. 9G.

As used herein, the term/phrase "worm-like" means any transport system that comprises plurality of elements arranged in a chain and that are able to change the relative orientation between adjacent chain elements.

Focusing now back to the treatment process. When scanning head 1710 (see FIG. 9B) finish the initial tissue mapping, and RFRD controller determined the skin penetration location, scanning head 1710 moves to passage 1044, grabs worm head 1296 and drive worm head 1296 to skin penetration point 1042. During this journey all worm connection elements are actuated to allow worm body crawling towards skin penetration point 1042. When head reach the skin penetration point 1042, a cannula is inserted to the skin to allow initial penetration of the worm through the skin. Worm then continues to be pushed in to the skin by scanning head 1710 until worm head 1296 reach the fat tissue. During this penetration stage worm head 1296 helps the penetration process by clearing the way and pushing aside cells as described later in connection with FIG. 9E and FIG. 9F.

When reaching the target fat tissue to be removed, worm continues to crawl back and forth in the fat tissue according to the plan prepared by RFRD controller using the measured 3D map of the fat tissues. During this stage, RFRD perform fat suction and, optionally, performing fat melting, materials injection and additional measurements.

Reference is now made to FIG. 9D. FIG. 9D illustrates cross-section view of the worm inside the target body organ. RFRD 104 is attached to the top layer of the skin, the epidermis layer 510. Under epidermis 510 reside the second layer of the skin, the dermis layer 522. Under dermis 522 resides the fat tissue 524 contains the fat cells. Blood vessels 526, nerve fibers 528 as well as nerve sensors 530 (pacinian corpuscles) are located inside fat tissue 524. Under fat tissue 524 resides the muscle tissue 532. To penetrate the skin scanning head 1710 is pushing cannula 1297 in to epidermis 520. After cannula 1297 stuck in the skin, scanning head 1710 pushes first worm head 1296 then worm elements 1292 one by one through the cannula in to the skin tissue. Until reaching the fat tissue, worm head 1296 is closed, i.e., do not suck tissue materials. Optionally, the tip of the worm head helps penetrating the dermis 522 as described later. When worm head 1296 reach the target tissue it may start suck fat cells. The worm may perform complex trajectory to avoid obstacles such as blood vessels 526, nerve large fibers 528 and nerve sensors 530. The trajectory is planned in order to suck the chosen volume of fat tissue 524. The trajectory on fat tissue 524 may be planed ahead with the aid of the 3D tissue mapping done at the beginning of treatment. Additionally or alternatively, using sensors, such as camera, on worm head 1296 the trajectory may be updated during suction in response to new data and/or locally better resolution data reading form worm head 1296.

When all fats planed to be removed from fat tissue 524 are collected, worm is pulled back in to RFRD 104. Worm connection elements 1294 are activated in a way that keeps the whole worm structure exactly in the planed trajectory. Finally, when worm head 1296 exit the body the worm is folded back in to cartridge 204. Cannula 1297 is pulled out as well and patient can detach RFRD 104 and dispose cartridge 204. Reference is now made to FIG. 9E and FIG. 9F. FIG. 9E illustrates isometric view of worm head 1296 when tip is closed. Worm head 1296 has a cylindrical shape with a sharp tip at the front. The tip is comprises from four flaps 1299. In FIG. 9E, flaps 1299 are closed and the sharp tip helps the worm to penetrate the tissue smoothly. In FIG. 9F, flaps 1299 are open and enable injection and suction operation. Optionally, flaps 1299 are transparent to allow camera reside inside worm head 1296 to see even when flaps 1299 are closed. Flaps 1299 are also used for penetration and sucking in the following ways: (1) during penetration, worm is moving forward and during the movement flaps 1299 gently and repeatedly opens half way to push cells and other tissue components aside and to clear the way of penetration; (2) during suction, when worm is moving forward flaps 1299 are repeatedly open to the maximum and then closed to capture and push the fat cells in to the worm suction tube.

Reference is now made to FIG. 9G. FIG. 9G illustrates a front view of worm head 1296. Worm head cylindrical case 2290 surrounds nine longitudinal zones. Those zones are not only maintained in worm head 1296, they are extended through worm elements 1292 and worm connection elements 1294 until the worm tail 1290. The center zone is suction tube 2292. Suction tube 2292 is a pipe resides in the center of the cylinder and extends through worm elements until worm tail. In worm tail 1290, suction tube 2292 is connected to the removed fat tank through connector 228 (see FIG. 9C). Optionally, inside suction tube 2292, exists suction elements that create suction forces and/or mechanically pushes the fat towards the worm tail. The other eight zones are located between suction tube 2292 and worm head cylindrical case 2290. Four 90 degrees spread zones are allocated for actuators. Flap actuators 2294 are used for the movement of the flaps. The actuators in worm head 1296 are used to open and close flaps 1299. In the same longitudinal zones of flap actuators 2294 and in each worm element 1292, a worm bending actuators are located (illustrated in FIG. 9H). Two cameras 1740 are located on the front of worm head 1296. Behind each camera 1740 there is a DC power cable. One cable carries the (+) polarity and the other carries the (−) polarity. The power cable pair feed all power consumers along the worm. In addition, power cable is used to carry digital communication between the RFRD controller and the worm actuators as well as the cameras 1740. Alternatively, wireless communication is used. The pair of cameras brings a stereoscopic view to the RFRD controller and is used to measure accurate distance of objects from the worm tip. Lightening the worm tip surrounding is done using fiber optic 1742. Additionally or alternatively, Fiber optic 1742 is used radiate strong light in order to melt the fat tissue in worm tip surrounding. An injection tube 1620 is located in the last lower zone. Injection tube 1620 injects materials such as anesthesia, melting and/or healing materials. Additionally or alternatively, Injection tube 1620 is used to inject additional medications. Drug delivery using such worm type device can be very accurate to target location from one hand and can deliver big molecules such as protein from the other hand so present invention may be used as an independent drug delivery system as well.

Figure 9H:
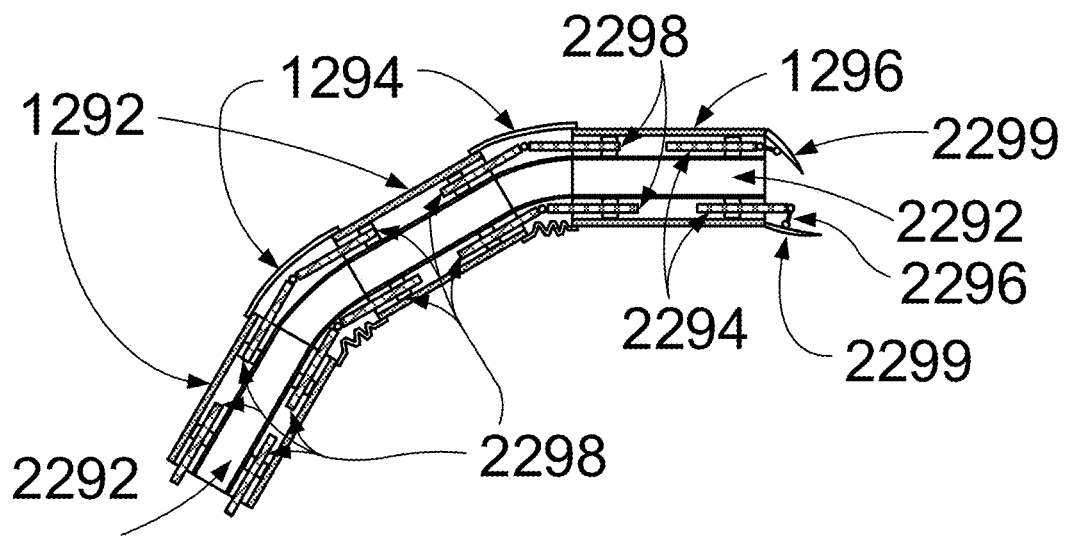

Reference is made now to FIG. 9H. FIG. 9H illustrate a cross-section E-E of the worm. Suction tube 2292 resides in the center of worm head 1296, worm elements 1292 and worm connection elements 1294. Flaps 1299 are moved by flap actuators 2294. Two out of for flap actuators 1294 are shown in this cross-section. Flap actuator 2294 comprises a screw-like rod sliding over a motor that spins the rod clock-wise or counter-clock-wise. The spinning pushes the rod towards the flap or pulls the rod backwards. Flap actuators 2294 is connected to flap 1299 using a double joint 2296 that transfer the linear movement of the rod to the angular movement of the flap. Optionally, the motor in flap actuator 2294 is an electric motor with the rod act as the rotor and the nut part act as a stator. Additionally or alternatively, flap actuators 2294 is electrostatic comb MEMS actuator or electromagnetic coil actuator.

On the left side of the worm head 1296 four worm bending actuators 2298 are located (two out of the four appears in the cross-section). In each worm element 1292 eight worm bending actuators 2298 are located (only four out of eight appears in the cross-section). Worm bending actuator is implemented in similar way to flap actuator 2294. Between each two adjacent elements, inside worm connection element 1294, four joint (only two appear on the figure) are located. The joints connect between the rods from both sides and enable the bending of the worm. Worm connection element case is flexible (as illustrated in the figure) to allow the bending of the worm as well.

In some cases, where the patient is suffering from significant overweight, removing fat cells that causes a reduction in the fat cell count, which is too high, is desirable. In prevention treatment in early stages of gaining weight, fat removal may better be done by removing fats without destroying existing fat cells. Although a very thin needles that will penetrate the cell membrane and pick triglyceride droplets from within the cells without destroying the cells is a possible option using nanotechnologies and MEMS techniques, such a delicate operation is less practicable, very expensive and very challenging in mass production. Instead, a different approach may be used.

As used herein, the term/phrase non-destructive fat removal means any fat removal that removes fat from the body, wherein the majority of the fat removal does not comes from removal or distraction of a complete fat cells.

Figure 10A:
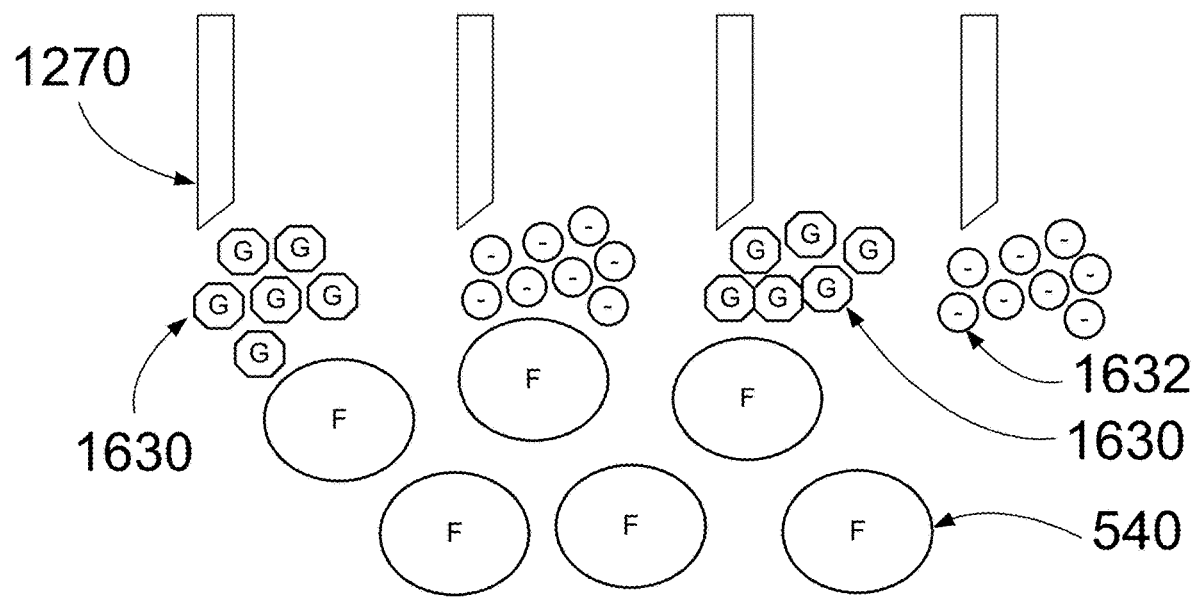
FIGS. 10A-10D are illustrations of exemplary embodiment of a non-destructive fat removal treatment in accordance with a preferred embodiment of the invention.

Reference is now made to FIG. 10A-FIG. 10D. FIG. 10A-FIG. 10D illustrate four stages of a non-destructive fat removal treatment. Reference is now made to FIG. 10A. In an exemplary embodiment of the invention, the injection subsystem injects to the fat tissue glucagon hormone 1630 via Needles 1270. Glucagon hormone 1630 is used in the human body to signal fat cells 540 in the fat tissue to breakdown the triglycerides stored in the fat cells to fatty acids and release them to the intercellular fluid which in turn diffused to the blood stream. In an exemplary embodiment of the invention, the fatty acids in the intercellular fluid are sucked by the residual fat removal device. In order to perform this selective suction the RFRD inject to the tissue an ionized compound 1632 that tends to bond with fatty acids. The compound may be a protein similar to the human fatty acid binding protein or preferably smaller molecule. An ionized version of Glycerol may be used. The mixture of glucagon hormone 1630 and ionized compound 1632 is injected to the fat tissue as illustrated in FIG. 10A. The mixture can be mixed before the injection and injected by all needles or some needle inject glucagon hormone 1630 and other inject ionized compound 1632 as illustrated in the figure.

Figure 10B:
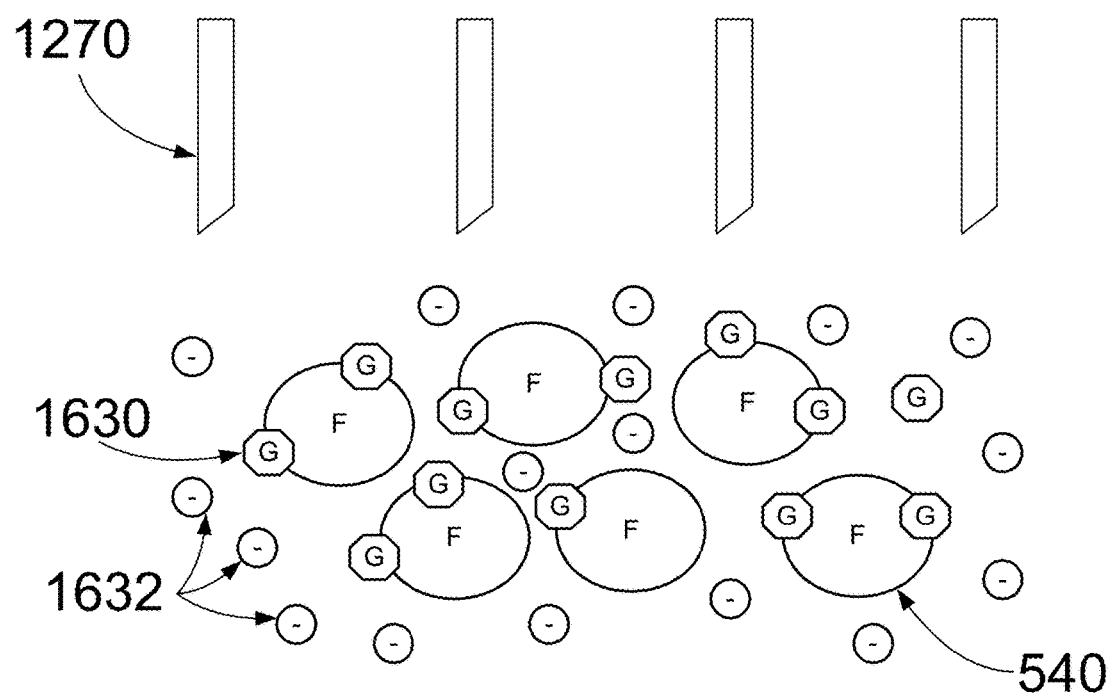

Reference is now made to FIG. 10B. After several minutes the mixture diffused in the intercellular fluid surround needles 1270. The intercellular fluid, in that stage, contains ionized compound 1632 and glucagon hormone 1630 that bonds to the glucagon receptors on the membranes of fat cells 540 as illustrated in the figure.

Figure 10C:
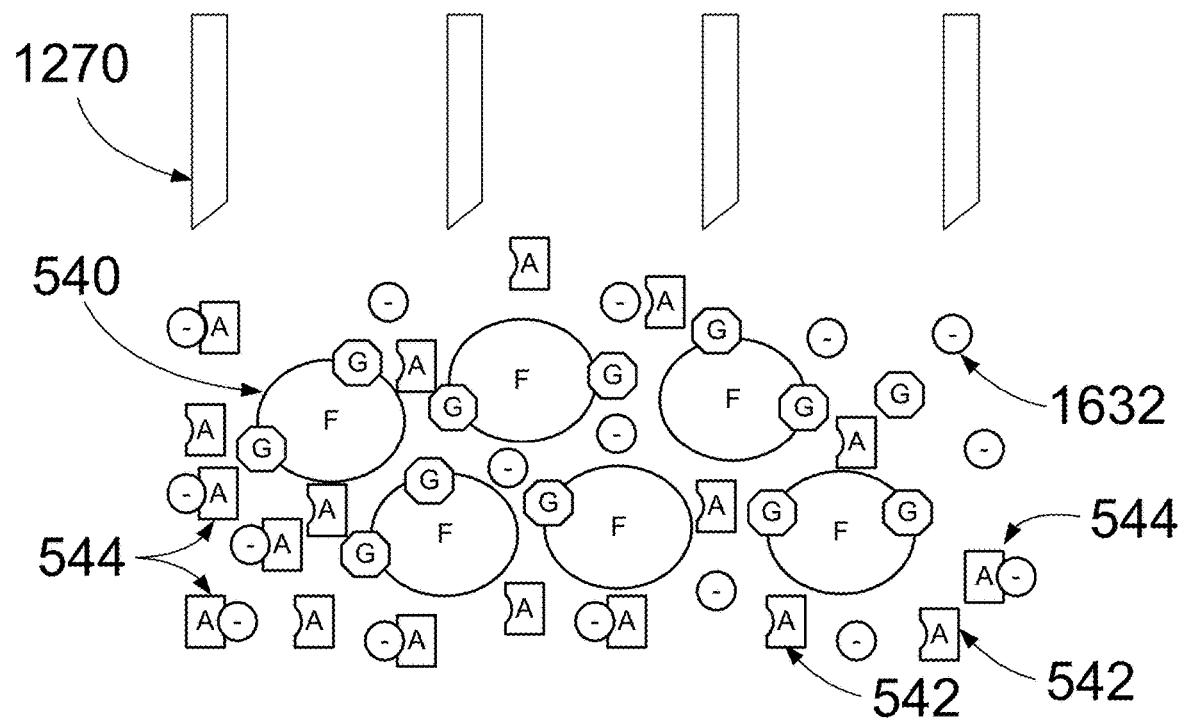

Reference is now made to FIG. 10C. Glucagon hormone 1630 signals fat cell to release fatty acid 542 to the intercellular. The fatty acid in the intercellular fluid bonds with the ionized compound 1632 and forms a new ionized molecule 544. As time goes by, more fatty acids 542 are released and more ionized molecules 544 are generated.

Figure 10D:
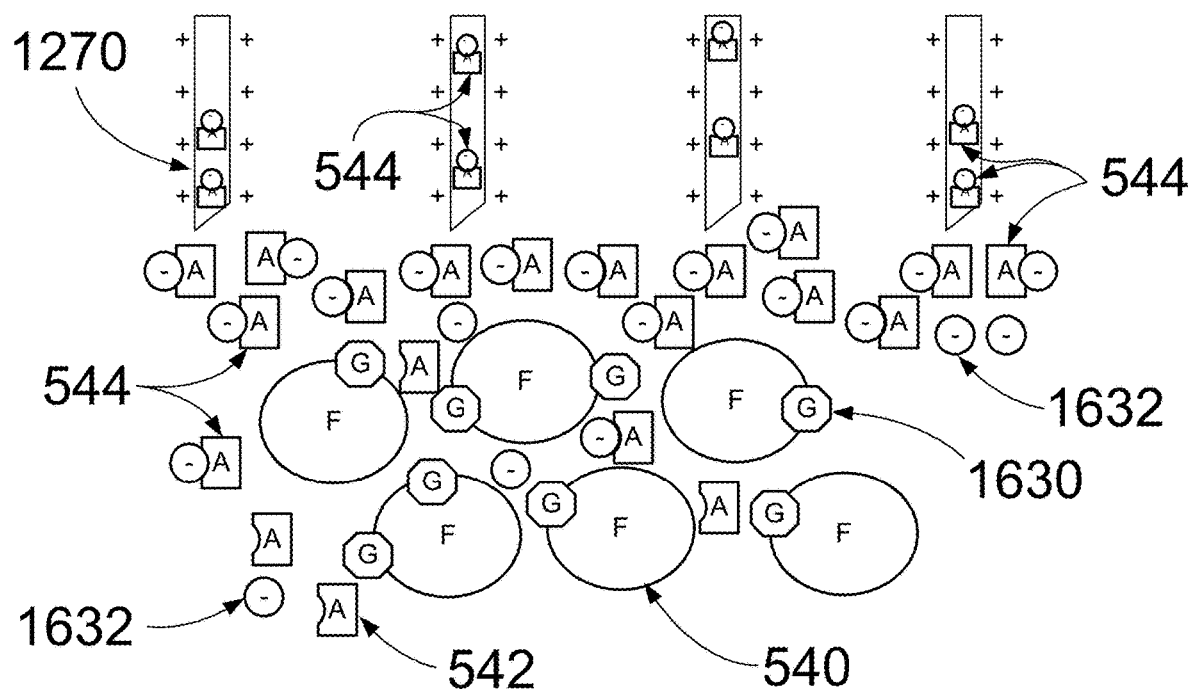

Reference is now made to FIG. 10D. In this stage, a positive electric potential is applied to needles 1270. The positive potential attracts ionized molecules 544 to Needles 1270 and the suction force sucks ionized molecules 544 to the removed fat tank in the RFRD. FIG. 10 illustrates a non-destructive fat removal using an embodiment similar to the one illustrated in FIG. 5. However, similar non-destructive fat removal methods may be implemented in other embodiments similar to the ones disclosed in the invention.

Alternatively, fat molecule removal may be performed on the blood stream instead of the fat tissue. Connecting the RFRD to the blood stream is more invasive and potentially more unpleasant or painful to patient, but it has several advantages. First, blood is much easier to suck and circulate due to its fluidity and its nature flow, i.e. the blood pressure in blood vessels. Second, blood contains several types of energy storing molecules, such as triglycerides, fatty acid, glucose, etc., that potentially can removed to balance the total energy accumulated. And last, it is inherently non-destructive treatment since in the blood the energy containing materials are in molecular form. RFRD device may remove any one of the energy containing molecules types that reside on the blood. Alternatively, a mixture of energy containing molecules types may be removed. Care should be taken not to remove too much of any specific molecule in order not to disrupts body normal metabolism. From the other hand, some patients have abnormal high level of fats molecule and/or glucose and removal of such molecule when such condition exists can have other healthy benefits on top of the fat removal to treat patient's obesity. One of the more interesting molecules in this case is the glucose molecule. It is well known that patients with type 2 diabetes suffer from high level of glucose that is very harmful for many organs and systems in the body. RFRD device that will monitor the glucose level and remove glucose from the blood stream when glucose levels are high, will help to balance those patients. Moreover, diabetes patients are treated with insulin, which one of the known side effects leads to gaining weight. Removal of glucose directly from the blood stream reduces the need to inject insulin.

As used herein, the term/phrase vascular fat removal means removal of energy containing molecules from the blood stream. Energy containing molecules include lipids (fats) including but not limited to fatty acids and triglycerides and carbohydrates including but not limited to glucose, fructose and ketones.

As used herein, the term/phrase energy containing molecules means any molecule that the human body cells are using as a source of energy or any molecule that the human body transfer to a molecule that the human body cells are using as a source of energy.

As used herein, the term/phrase target energy containing molecules means the energy containing molecules that are targeted for removal by a residual fat removal treatment.

As used herein, the term/phrase energy containing materials means materials that include energy containing molecules such as fat cells, fat tissue, intercellular fluid or blood.

Figure 11:
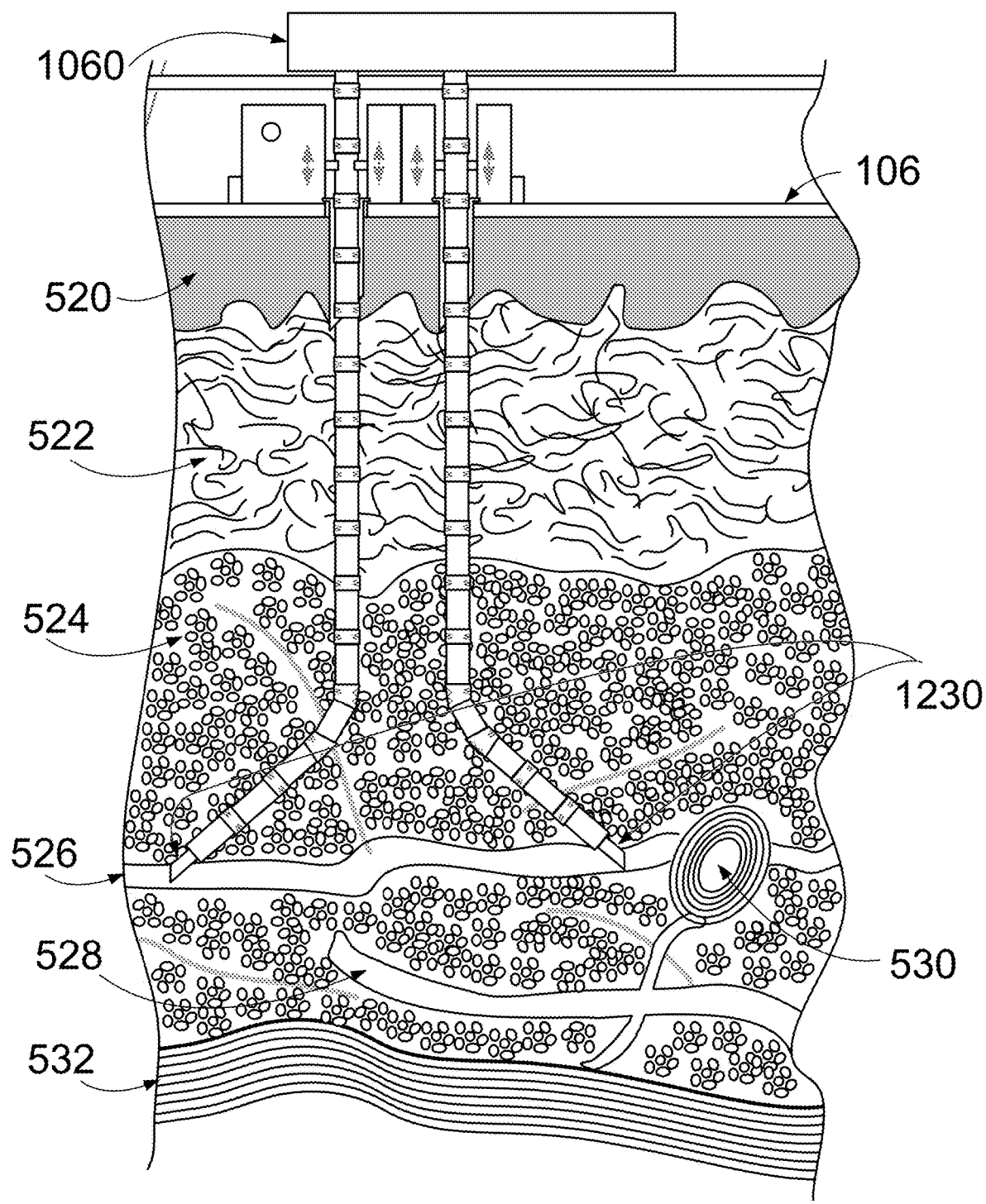
FIG. 11 is a cross-section view of non-destructive, vascular fat removal version of fat removal device during in body treatment, in accordance with a preferred embodiment of the invention.

Reference is now made to FIG. 11. FIG. 11 illustrates a cross-section view of vascular fat removal version of residual fat removal device during in body treatment. RFRD 106 that perform vascular fat removal, i.e., removes fat or energy storage molecules from the blood stream. RFRD 106 is using worms-like transport subsystem similar to the one described in FIG. 5D. Two worms are used one for blood inlet and the other for blood outlet. Worms are directed by RFRD controller to the target blood vessel 526. Target blood vessel 526 is located during the initial measurement stage using the ultrasound measurement subsystem. During penetration cameras on worm tips can help to accurately approach blood vessel 526. The worm heads tip contains needle 2230 to sharply penetrate the blood vessel when worm head reach the target blood vessel. Blood flow from the blood vessel to fat remover 1060. Fat remover 1060 is the element that removes energy containing molecules from the blood and transfers those molecules to the removed fats tank. Additionally or alternatively, RFRD 106 may use two different blood vessels for blood inlet and blood outlet. Optionally, RFRD 106 uses both veins and arteries. In an exemplary embodiment of the invention, RFRD 106 blood inlet is from artery and blood outlet is to vein. Fat remover 1060 is implemented by using a special membrane that allows only the target energy containing molecules to pass through the fat remover membranes. Optionally, fat remover 1060 contain a measurement subsystem that measure the concentration target energy containing molecules and optionally remove the target energy containing molecules only if the concentration is above certain threshold. Optionally, fat remover 1060 measures the amount of target energy containing molecules removed and RFRD controller stops the fat removal when the target amount is reached.

The embodiment described in FIG. 11 is extracting the energy containing molecules from the blood through the skin into an external device. The waste products are further extracted from the device. To avoid the daily burden of attach and detach as well as dealing with the waste, alternatively, the RFRD is an implanted device that is connected to the blood stream from one side and to the urinary system from the other side is another embodiment of the invention. In an exemplary embodiment of the invention the implant is located in the abdominal cavity near one of the kidneys, with blood intake from the renal artery and blood outlet to the renal vein. The extract energy containing molecules are spilled to the ureter and mixed with the urine and extracted out during urination.

Figure 13A:
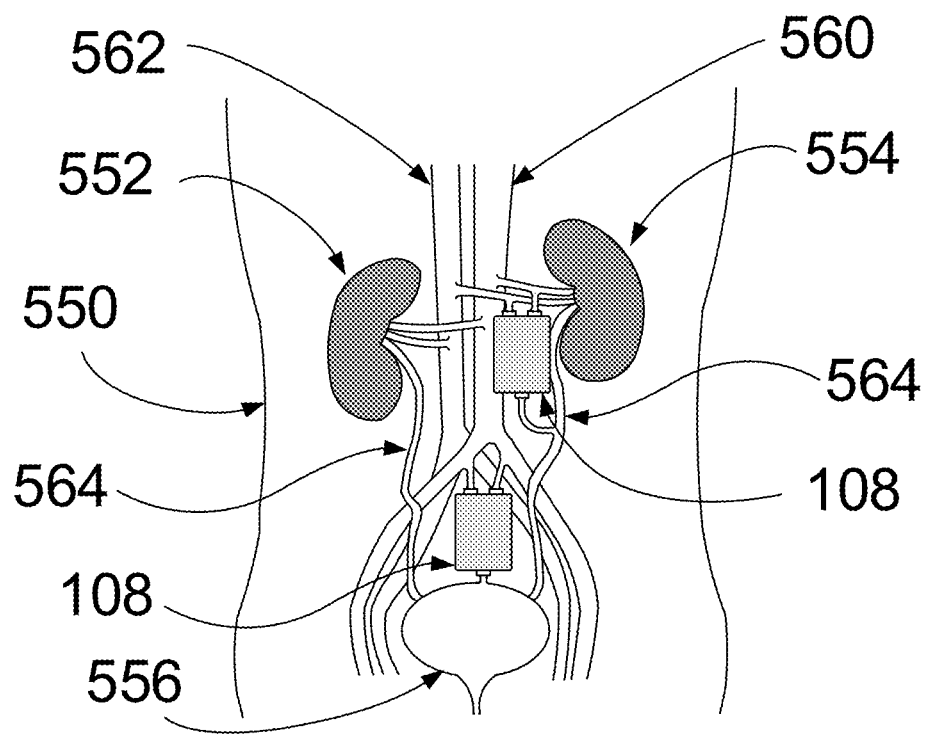
FIGS. 13A-13B are illustrations of exemplary embodiment of an implant version of fat removal device in accordance with a preferred embodiment of the invention.

Reference is now made to FIG. 13A. FIG. 13A illustrates an internal view of abdomen 550. In the Figure, right kidney 552, left kidney 554 and urinary bladder 556 are illustrated. The blood vessels in the figure include varies arteries that split from the descending aorta 560 as well as several veins that are drained to Inferior vena cava 562. The kidneys 552 and 554 are connected to the urinary bladder 556 via ureters 564. Implant 108 is the residual fat removal device, RFRD, in this embodiment. Two alternative locations for implant 108 are illustrated in the figure. In the top option implant 108 is located aside of the left kidney 554. The blood intake is taken from the renal artery and blood outlet is exhausted into the renal vein. The energy containing molecules waste is spilled to the left ureter 564.

The bottom option implant 108 is located on top of urinary bladder 556. In this exemplary embodiment, the blood intake is taken from the left iliac artery and the blood outlet is exhausted to the right iliac artery. The energy containing molecules waste is spilled directly to the urinary bladder 556. Many other alternative locations for implant are feasible. Blood inlets and outlets can be connected to different arteries and veins. Blood vessel inlet outlet pair may be artery-vain, artery-artery or vain-vain. The waste outlet can be connected in any point in ureters 564 as well as directly to the urinary bladder 556.

Figure 13B:
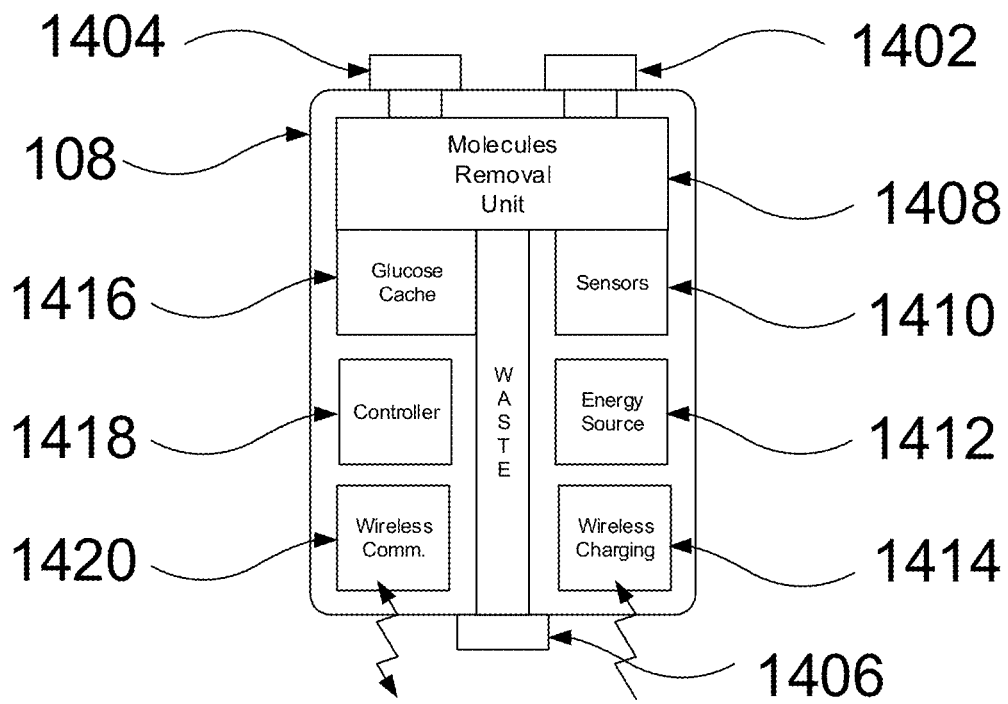

Reference is made now to FIG. 13B that illustrates a conceptual block diagram of implant 108. Implant 108 comprises three ports: blood intake 1402, blood outlet 1404 and waste outlet 1406. Blood intake 1402 is connected to energy containing molecules removal unit 1408 which is able to extract specific molecules such as lipids and carbohydrates from the blood stream. In an exemplary embodiment of the invention, molecules removal unit 1408 is design to remove a specific energy containing molecule such as glucose or fatty acid or triglyceride, etc. Alternatively, molecules removal unit 1408 is design to remove simultaneously several types of energy containing molecules. In an exemplary embodiment of the invention, molecules removal unit 1408 have a primary filtration process that first filters the small molecules so all blood cells, hormones, protein and other big molecule that are not target to extracted are carried out in the blood stream to outlet 1404 and not entered the secondary filtering and extraction process. In an exemplary embodiment of the invention, molecules removal unit 1408 use a selective membranes to extract the desired molecules from the blood stream. In an exemplary embodiment of the invention, molecules removal unit 1408 use electric and/or magnetic fields and/or mechanical force to sort and extract the desired molecules. The extracted molecules are exhausted from implant 108 through waste outlet 1406. In contact to the blood flow in the molecules removal unit 1408, a sensors unit 1410 is optionally installed. Sensors unit 1410 monitors the concentration of different molecules in the blood stream. Several molecules types are monitored. The target for extraction molecules are monitored, If the concentration level of any molecule type is lower then a threshold, molecules removal unit 1408 will not extract the specific molecule type. Optionally, other molecules in the blood steam are monitored. Implant 108 includes a controller 1416 that manage the operation of implant 108. The controller 1416 reads the sensors 1410 and commands molecule removal unit 1408 when and in which rate to extract the energy containing molecules. Controller 1418 is connected to wireless communication unit 1420. Controller 1418 sends data to a patient information system (not shown in the Figure). Using a remote control patient can communicate with controller 1418 and send commands to implant 108. Commands can be disable/enable, set the amount of extraction, set thresholds etc. Optionally, Controller 1418 sends sensors 1410 readings to the patient information system. Optionally, Controller 1418 sends log information such as the history of the amount of molecules that have been extracted to the patient information system.

To allow implant 108 operation and active extraction (i.e., extraction of molecules with the aid of external forces such as electric, magnetic, heat or mechanical forces or a combination of those) an energy source 1412, e.g., chargeable battery is used. In a preferred embodiment of the invention, energy source 1412 is charged by induction type wireless charging unit 1414. Optionally or alternatively, energy source 1412 charged by extracting power from the blood stream or the body heat.

Implant type RFRD such as illustrated in FIG. 13B is very well suited for diabetes patient. Since the implant is always in place and since it monitors the glucose level which is one of the most concentrated target energy molecule in the blood, the implant can extract glucose whenever glucose rate is higher the normal value. In this way, not only that it help the patient to get slimmer, the sugar level is also moderated which is very important to diabetes patient. Most diabetes patients (type II diabetes) are also overweight or obese so such an implant solves two problems in one device. Another important problem that can be solved by implant 108 is events of hypoglycemia. Diabetes patients take measures such as medication and insulin injection to reduce glucose level in the blood. However, the treatment may lead to hypoglycemia, i.e., lower then allowed concentration of glucose on the blood. Hypoglycemia is very dangers situation that lead to fainting and even death. Optionally, in a preferred embodiment of the invention, implant 108 contains a glucose cache 1416. Glucose cache stores some of the extracted glucose molecule in temporary storage. If a low glucose level is detected by sensors 1410, glucose cache 1416 injects some glucose back to the blood stream and prevents hypoglycemia condition.

In a similar way to glucose managing and moderating, in a preferred embodiment of the invention, implant 108 is managing and moderating lipids level in the blood stream to prevent variety of heart and blood vessel diseases such as heart attack and atherosclerosis.

Optionally, the extraction of the energy containing molecules can be done by stimulating the fat cell to release the fatty acids to the intercellular fluid and promote a chemical reaction that yield non toxic and less energetic products that can be carried by the blood and extracted from the body using the urine system or the respiratory system.

In an exemplary embodiment of the invention, a medical device, i.e. the RFRD, preferably a patch similar to the one illustrated in FIGS. 8 and 10 is used to generate fatty acids chemical reactions in the intercellular fluid of the fat tissue. Using glucagon hormone injection to the fat tissue, the device stimulates the fat cells to release fatty acid. The fatty acid is a long chain of carbon atoms bound to each other and each carbon atom bound to two or three hydrogen atoms as well. The chemical energy stored in those molecules is exploited in the body by a complex multi-stage reaction that occurs inside the cells with the aid of enzymes. There are many ways to performs chemical reaction with the fatty acid. One well known chimerical reaction of carbon chain molecules is a complete combustion. A complete combustion chimerical reaction release energy and yield water and carbon dioxide. For example, three carbon chain combustion is $C_3H_8+7O_2 \rightarrow 3CO_2+4H_2O$. The products, carbon dioxide and water, are both non toxic and are extracted from the body via the urinary system and the respiratory system respectively.

In an exemplary embodiment of the invention, the RFRD promote in the intercellular fluid of the fat tissue a fatty acid chemical reaction that yield non toxic non usable energy containing molecules. Alternatively, the chemical reaction products contain molecules that contain less total usable energy. For example, shorten the fatty acid chain by bounding the last carbon link and its hydrogen atoms in the fatty acid chain to a small non toxic, non energy containing molecules.

In an exemplary embodiment of the invention, the RFRD promote in the intercellular fluid of the fat tissue fatty acid chemical reactions by providing necessary compounds to participate in the chemical reaction, e.g., oxygen, nitrogen, metal atoms, ions, etc.

In an exemplary embodiment of the invention, the RFRD promote in the intercellular fluid of the fat tissue fatty acid chemical reactions by providing a catalyzing compounds or enzymes to enable the chemical reaction or accelerate the chemical reaction rate.

In an exemplary embodiment of the invention, the RFRD promote in the intercellular fluid of the fat tissue fatty acid chemical reactions by providing additional energy to the fat tissue intercellular fluid to accelerate that chemical reaction rate. The energy could be in the form of heat, RF radiation, light (visible, UV or IR) vibration, ultrasound waves, etc. The frequency of the waves, when applied, as well as the modulation frequency is set to a specific frequency that is best absorbs by the fatty acid molecule and hence most accelerate that chemical reaction rate.

Reference is now made to FIG. 14. FIG. 14A-FIG. 14D illustrate a preferred embodiment of the invention that promotes fatty acid chemical reactions in the intercellular fluid of the fat tissue. Reference is now made to FIG. 14A. In an exemplary embodiment of the invention, the injection subsystem injects to the fat tissue glucagon hormone 1630, reagent 1634 and catalyst 1636 via needles 1270. In FIG. 14A, glucagon hormone 1630, reagent 1634 and catalyst 1636 are injected through different needles 1270 but alternatively, a mixture of all compounds can be injected through all needles 1270. Optionally, reagent 1634 is a mixture of several reagents 1634. Optionally, catalysts 1636 are a mix of several catalysts. Reagent 1634 can be an element, a compound or any molecule that are target to bond with the fatty acid. Catalyst 1636 can be an element, a compound, an enzyme or any molecule that catalyze the reaction. The fat tissue contains fat cells 540 and capillary blood vessel 546. The volume between fat cells 540 and surround capillary 546 contains intercellular fluid.

Figure 14A:
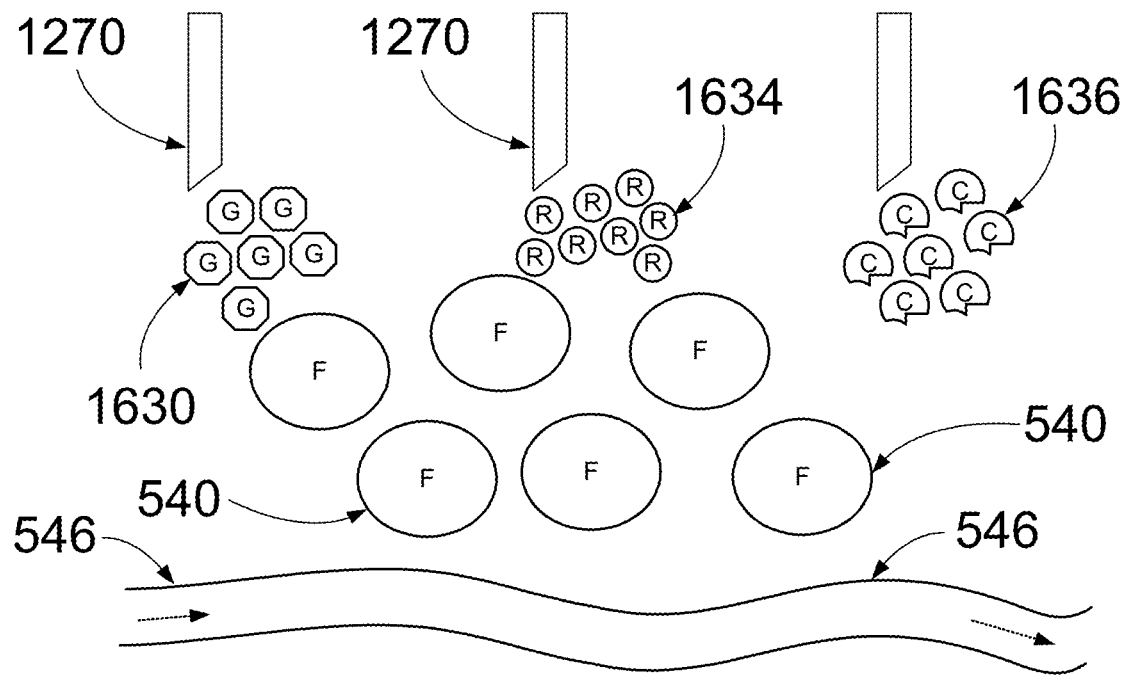
FIGS. 14A-14D are illustrations of exemplary embodiment of a non-destructive fat removal treatment that decompose fatty acid using a chemical reactions in the intercellular fluid of the fat tissue in accordance with a preferred embodiment of the invention.
Figure 14B:
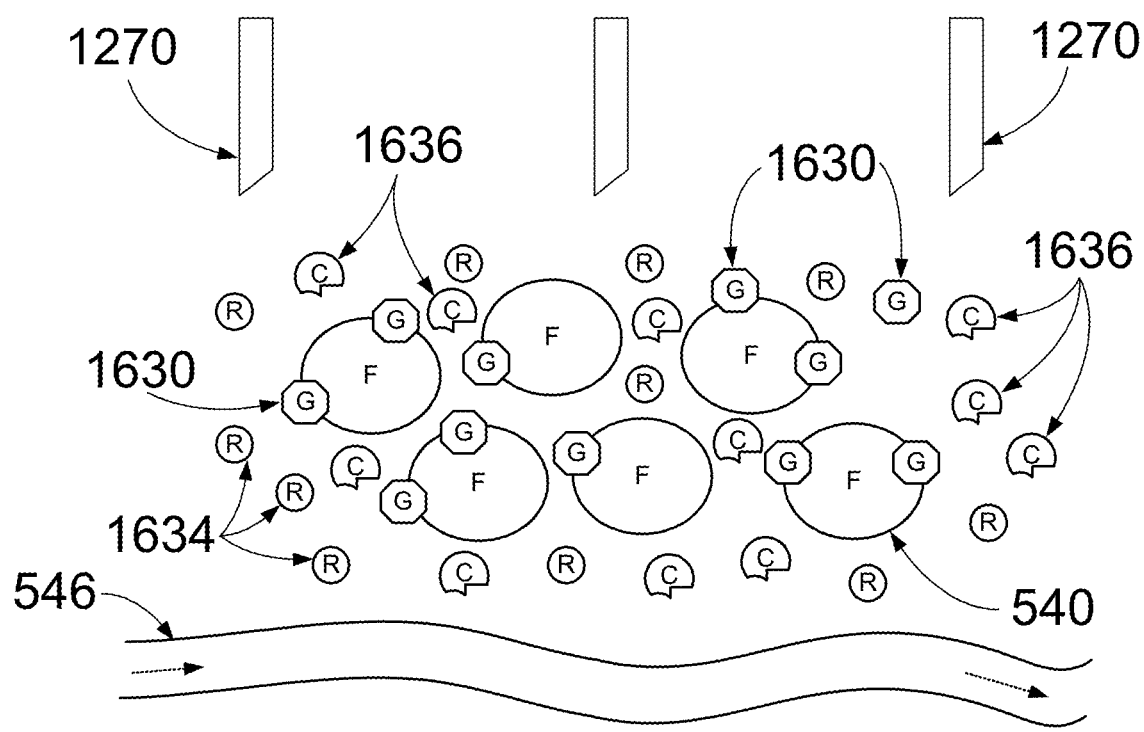

Reference is now made to FIG. 14B. After some time the injected mixture diffused in the intercellular fluid adjacent to needles 1270. The intercellular fluid, in that stage, contains reagent 1634, catalysts 1636 and glucagon hormone 1630.

Some of glucagon hormone 1630 bonds to the glucagon receptors on the membranes of fat cells 540 as illustrated in the figure.

Figure 14C:
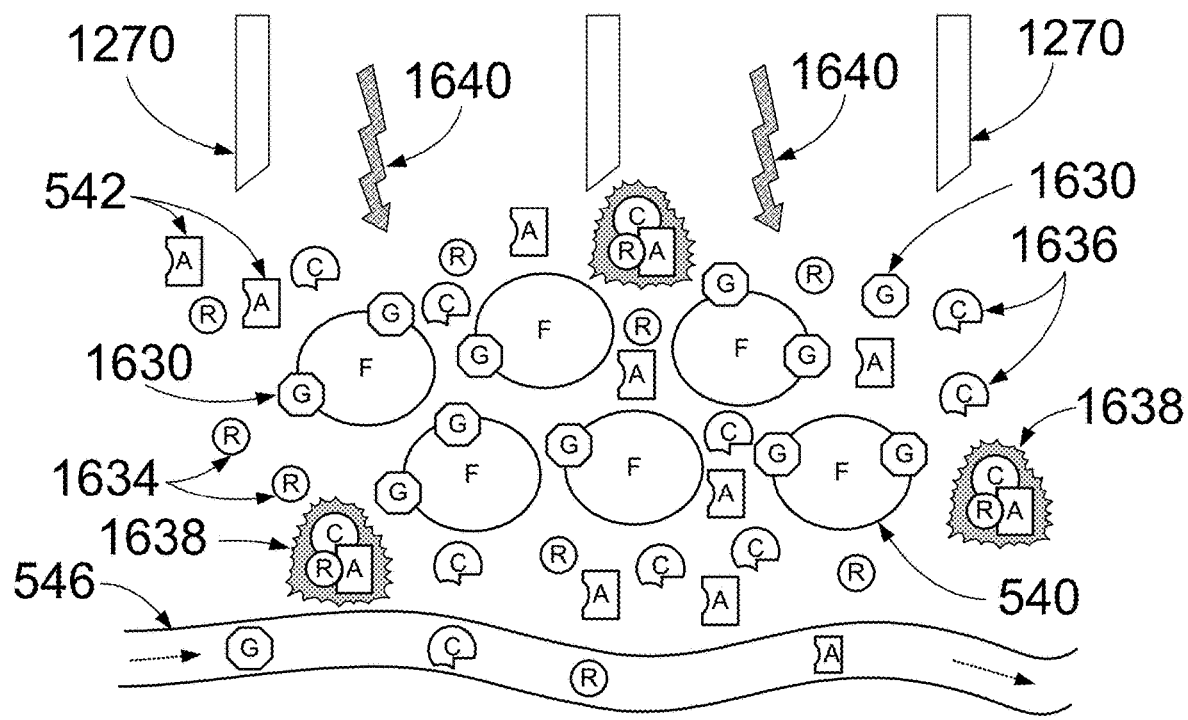

Reference is now made to FIG. 14C. In respond to the glucagon hormone 1630 signals, fat cells 540 secrete fatty acids 542. Fatty acids 542 together with reagent 1634 and catalysts 1636 perform a chemical reaction 1638. Optionally, additional energy 1640 is radiated, conducted or transferred to the fat tissue to promote the reaction. Alternatively, in a preferred embodiment of the invention, reagent 1634 is already exists in the intracellular fluid and is not injected by the RFRD. Alternatively, in a preferred embodiment of the invention, catalyst 1636 is not necessary to promote the chemical reaction 1638 and is not injected by the RFRD.

Figure 14D:
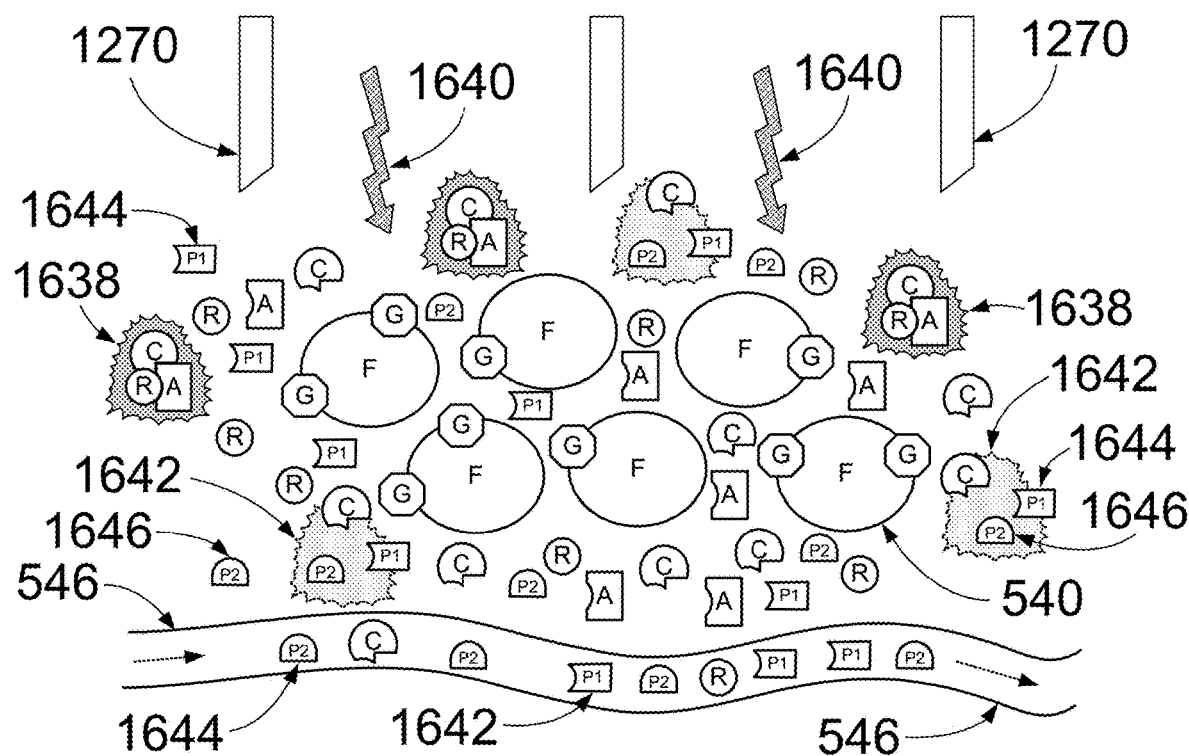

Reference is now made to FIG. 14D. After chemical reaction completion 1642, products 1644 and 1646 are formed. Products 1644 and 1646 are diffused in the intercellular fluid and also diffused into capillary 546 where they are carried away with the blood stream to the urine system or the respiratory system where they are removed out from the body. The number of different chemical reaction products may be more then two. In the case where some of the products are not a waste products the body may "recycle" those product molecules store them, use them or rebuild from them other molecules. According to the preferred embodiment of the invention, the total products of the chemical reaction contains less calories the original fatty molecule so overall a weight reduction will be accomplished.

It is expected that during the life of a patent maturing from this application many relevant micro robotics, nano technologies and medical and chemical technologies will be developed and the scope of the terms used is intended to include all such new technologies a priori.

The terms "comprises", "comprising", "includes", "including", "having" and their conjugates mean "including but not limited to".

As used herein, the singular form "a", "an" and "the" include plural references unless the context clearly dictates otherwise. For example, the term "a compound" or may include a plurality of compounds, including mixtures thereof It is appreciated that all mechanical and moveable elements described in the invention may be implemented in many ways, for example MEMS actuators may be implemented in electrostatic electromagnetic and thermal way with different geometries. In additions many emerging miniatures techniques for actuators and motors may be used.

It is appreciated that all management, processing and control elements described in the invention may be implemented in many ways, for example a micro controller, micro processor digital signal processor or a combination of those may be used.

It is appreciated that residual fat removal device design features like shape, material used, user interface and internal architecture may be implemented in many ways.

Whenever a numerical range is indicated herein, it is meant to include any cited numeral (fractional or integral) within the indicated range. The phrases "ranging/ranges from" a first indicate number "to" a second indicate number is used herein is meant to include the first and second indicated numbers and all the fractional and integral numerals therebetween.

As used herein, the term "obesity" includes any condition of excessive weight including but not limited to a condition of body mass index (BMI) of over 25.

As used herein, the term "obesity treatment" includes abrogating, substantially inhibiting, slowing or reversing the progression of obesity, substantially ameliorating clinical or aesthetical symptoms of obesity or substantially preventing the appearance of clinical or aesthetical symptoms of obesity.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A medical device for treatment of overweight or obesity comprising:
 a case with an opening;
 an attachment subsystem;
 a suction subsystem;
 a disposable cartridge further comprising:
  a transport subsystem comprising one or more hollow needles that are configured to penetrate a patient's target body organ skin; and
  a tank;
wherein the medical device is configured to be attached to a patient's target body organ skin by the attachment subsystem, and using the suction subsystem to remove up to 100 grams of energy containing materials from the patient's target body organ to the tank, the case is configured to surround and hold the disposable cartridge; the tank and needles are resided inside the disposable cartridge that is configured to be fitted into the opening of the case of the medical device, and the disposable cartridge is configured into the inserted to the medical device before the treatment and to be disposed after the treatment.

2. The medical device of claim 1, wherein said medical device further comprises a management subsystem that controls the treatment.

3. The medical device of claim 2, wherein the management subsystem communicates with the patient via one or more of or a combination of (1) button, (2) indicator, (3) display, and (4) communication link.

4. The medical device of claim 3, wherein the management subsystem is configured to instruct the patient of, at least, the time for attachment or the attachment area for the next said medical device attachment.

5. The medical device of claim 3, wherein completion of the treatment is indicated to the patient.

6. The medical device of claim 2, wherein the management subsystem comprises one or more of or a combination of (1) processor, (2) controller, (3) analog circuit, (4) digital circuit, and (5) computerized system.

7. The medical device of claim 1, wherein said medical device further comprises an injection subsystem configured to inject materials to the patient's target body organ.

8. The medical device of claim 7, wherein said injection subsystem is configured to inject one of or a combination of (1) anesthetizing materials, (2) melting materials, (3) glucagon hormone or materials that promote release of fat from the patient's target body organ fat cells, (4) filling materials, and (4) healing materials.

9. The medical device of claim 7, wherein the measurement subsystem measures one of or a combination of (1) a thickness of the skin tissues, (2) a thickness of the fat tissues, (3) a depth of penetration, (4) blood vessels locations, and (4) an amount of the removed energy containing materials.

10. The medical device of claim 1, wherein the transport subsystem comprises array of micro needles.

11. The medical device of claim 10, wherein the array of micro needles is fabricated on a semiconductor die.

12. The medical device of claim 10, wherein the micro needles are movable by MEMS actuators.

13. The medical device of claim 10, wherein the micro needles are folded in said medical device before treatment and are opened during the treatment.

14. The medical device of claim 1, wherein said medical device further comprises a melting subsystem that is configured to perform liquefying of fats or breaking fat tissues or fat cell to a smaller, non-connected, components or particles in the patient's target body organ fat tissue.

15. The medical device of claim 14, wherein said melting subsystem is configured to perform the melting by heating patient's target body organ fat tissue using one of or a combination of (1) electric current, (2) Ultrasound waves, (3) RF waves, and (4) light waves.

16. The medical device of claim 14, wherein said melting subsystem is configured to perform the melting by injection of melting materials to patient's target body organ.

17. The medical device of claim 1, wherein said transport subsystem comprises of worm-like arm that penetrates the skin and crawls into the patient's target body organ fat tissue.

18. The medical device of claim 17, wherein worm-like arm comprises a plurality of worm elements.

19. The medical device of claim 1, wherein the needles are configured to be actuated by actuators that reside inside of the medical device and outside of the disposable cartridge.

20. The medical device of claim 1, wherein the device shape is rectangular or circular.

21. The medical device of claim 1, wherein said attachment subsystem comprises any one or more of or a combination of a strip, an elastic element, a Velcro, and an adhesive material.

22. The medical device of claim 1, wherein said needles length is between 4 millimeters to 6 millimeters and said needle width is less than 1 millimeter.

23. The medical device of claim 1, wherein said medical device comprises controller and wherein the controller is controlling the insertion of said needles at different times.

24. The medical device of claim 1, wherein the needles are configured to penetrate and retract the skin using one or more or any combination of a motor, an actuator, and a spring.

25. The medical device of claim 1, wherein said suction subsystem comprises one or more pumps.

26. The medical device of claim 1, wherein said suction subsystem uses for suction mechanical actuation that pushes energy containing materials through the transport system.

27. The medical device of claim 1, wherein said suction subsystem uses for suction any one of or a combination of (1) a low pressure, (2) capillary forces, (3) electric forces, and (4) mechanical forces.

28. The medical device of claim 1, wherein said medical device is configured to attach to the patient's target body organ skin and the medical device attachment area is a more than 1 squared centimeter and less than 100 squared centimeters.

29. The medical device of claim 1, wherein said medical device further comprises a measurement subsystem that measure a characteristics of the patient's target body organ or a state of the treatment.

30. The medical device of claim 1, wherein said medical device is configured to enable performing of attachment and detachment of said medical device by the patient himself.

31. The medical device of claim 1, wherein said energy containing materials are fat cells.

32. The medical device of claim 1, wherein said energy containing materials are fatty acids molecules.

33. The medical device of claim 1, wherein said energy containing materials are glucose molecules.

34. The medical device of claim 1, wherein said medical device removes said energy containing materials from the blood stream.

* * * * *